US007681256B2

(12) United States Patent
Fullerton et al.

(10) Patent No.: US 7,681,256 B2
(45) Date of Patent: Mar. 23, 2010

(54) CORRELATED MAGNETIC MASK AND METHOD FOR USING THE CORRELATED MAGNETIC MASK

(75) Inventors: Larry W. Fullerton, New Hope, AL (US); Mark D. Roberts, Hunstville, AL (US)

(73) Assignee: Cedar Ridge Research, LLC., New Hope, AL (US)

( * ) Notice: Subject to any disclaimer, the term of this patent is extended or adjusted under 35 U.S.C. 154(b) by 0 days.

(21) Appl. No.: 12/479,074

(22) Filed: Jun. 5, 2009

(65) Prior Publication Data

US 2009/0288241 A1 Nov. 26, 2009

Related U.S. Application Data

(63) Continuation-in-part of application No. 12/476,952, filed on Jun. 2, 2009.

(51) Int. Cl.
*A42B 1/06* (2006.01)

(52) U.S. Cl. ....................... 2/410; 2/426; 2/439; 2/448; 335/285

(58) Field of Classification Search ..................... 2/4–9, 2/15, 410, 426–454; 335/285
See application file for complete search history.

(56) References Cited

U.S. PATENT DOCUMENTS

| | | | |
|---|---|---|---|
| 381,968 | A | 5/1888 | Tesla |
| 4,079,558 | A | 3/1978 | Gorham |
| 4,547,756 | A | 10/1985 | Miller et al. |
| 4,903,349 | A * | 2/1990 | Arai .............................. 2/421 |
| 5,383,049 | A | 1/1995 | Carr |
| 5,631,093 | A | 5/1997 | Perry et al. |
| 5,956,778 | A | 9/1999 | Godoy |
| 5,983,406 | A | 11/1999 | Meyerrose |
| 6,072,251 | A | 6/2000 | Markle |
| 6,115,849 | A | 9/2000 | Meyerrose |
| 6,275,778 | B1 | 8/2001 | Shimada et al. |
| 6,457,179 | B1 | 10/2002 | Prendergast |
| 6,607,304 | B1 | 8/2003 | Lake et al. |
| 6,720,698 | B2 | 4/2004 | Galbraith |
| 6,847,134 | B2 | 1/2005 | Frissen et al. |

(Continued)

FOREIGN PATENT DOCUMENTS

| | | |
|---|---|---|
| FR | 823395 | 1/1938 |

OTHER PUBLICATIONS

"BNS Series-Compatible Series AES Safety Controllers"pp. 1-17, http://www.schmersalusa.com/safety_controllers/drawings/aes.pdf (downloaded on or before Jan. 23, 2009).

(Continued)

*Primary Examiner*—Ramon M Barrera
(74) *Attorney, Agent, or Firm*—Wiliam J. Tucker

(57) ABSTRACT

A mask is described herein that uses correlated magnets which enable a person to easily secure and remove the mask to and from their head. Some examples of such a mask include a scuba mask, a welding mask, a fencing mask, a goalie mask, a paint mask, a paintball mask, a catcher's mask, a ski mask, a goalie mask, an oxygen mask, a surgical mask, a face shield, a filter mask, a theatrical mask, a costume mask, a continuous positive airway pressure (CPAP) mask.

21 Claims, 16 Drawing Sheets

1022 1022 1016 1010 1018 1022 1022 1018 1018a 1023 1018a 1022 1022 1018a 1020 1018 1024 1014 1015 1020a 1022 1022 1013 1018

U.S. PATENT DOCUMENTS

| | | | | |
|---|---|---|---|---|
| 6,862,748 | B2 | 3/2005 | Prendergast | |
| 7,066,778 | B2 | 6/2006 | Kretzschmar | |
| 7,246,384 | B2 * | 7/2007 | Bentz | 2/421 |
| 7,362,018 | B1 | 4/2008 | Kulogo et al. | |
| 7,444,683 | B2 | 11/2008 | Prendergast et al. | |
| 7,568,797 | B2 * | 8/2009 | Hibbs, Jr. | 351/158 |
| 2006/0066428 | A1 | 3/2006 | McCarthy et al. | |
| 2006/0189259 | A1 | 8/2006 | Park | |
| 2006/0290451 | A1 | 12/2006 | Prendergast et al. | |
| 2007/0216095 | A1 * | 9/2007 | Jacobs | 273/288 |
| 2008/0186683 | A1 | 8/2008 | Ligtenberg et al. | |
| 2008/0272868 | A1 | 11/2008 | Prendergast et al. | |
| 2009/0044315 | A1 * | 2/2009 | Belanger et al. | 2/414 |

OTHER PUBLICATIONS

"Magnetic Safety Sensors"pp. 1-3, http://farnell.com/datasheets/6465.pdf (downloaded on or before Jan. 23, 2009).

"Series BNS-B20 Coded-Magnet Sensor Safety Door Handle" pp. 1-2, http://www.schmersalusa.com/catalog_pdfs/BNS_B20.pdf (downloaded on or before Jan. 23, 2009).

"Series BNS333 Coded-Magnet Sensors with Integrated Safety Control Module"pp. 1-2, http://www.schmersalusa.com/machine_guarding/coded_magnet/drawings/bns333.pdf (downloaded on or before Jan. 23, 2009).

* cited by examiner

300
Barker - 7 code = + 1 + 1 + 1 - 1 - 1 + 1 - 1
302a
302b
302c
302d
302e
302f
302g
304
306
308a
308b
308c
308d
308e
308f
308g
310-1
1R = -1
310-2
1A+1R = 0
310-3
1A+2R = -1
310-4
2A+2R = 0
310-5
2A+3R = -1
310-6
3A+3R = 0
310-7
7A = 7
310-8
3A+3R = 0
310-9
2A+3R = -1
310-10
2A+2R = 0
310-11
1A+2R = -1
310-12
1A+1R = 0
310-13
1R = -1

FIG. 3B
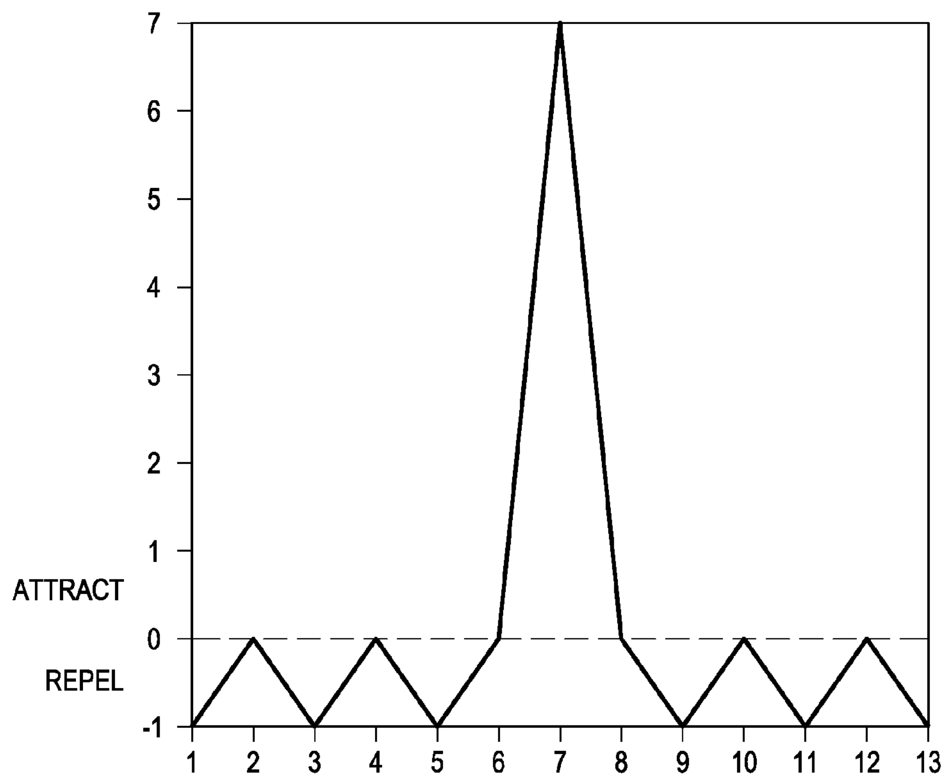
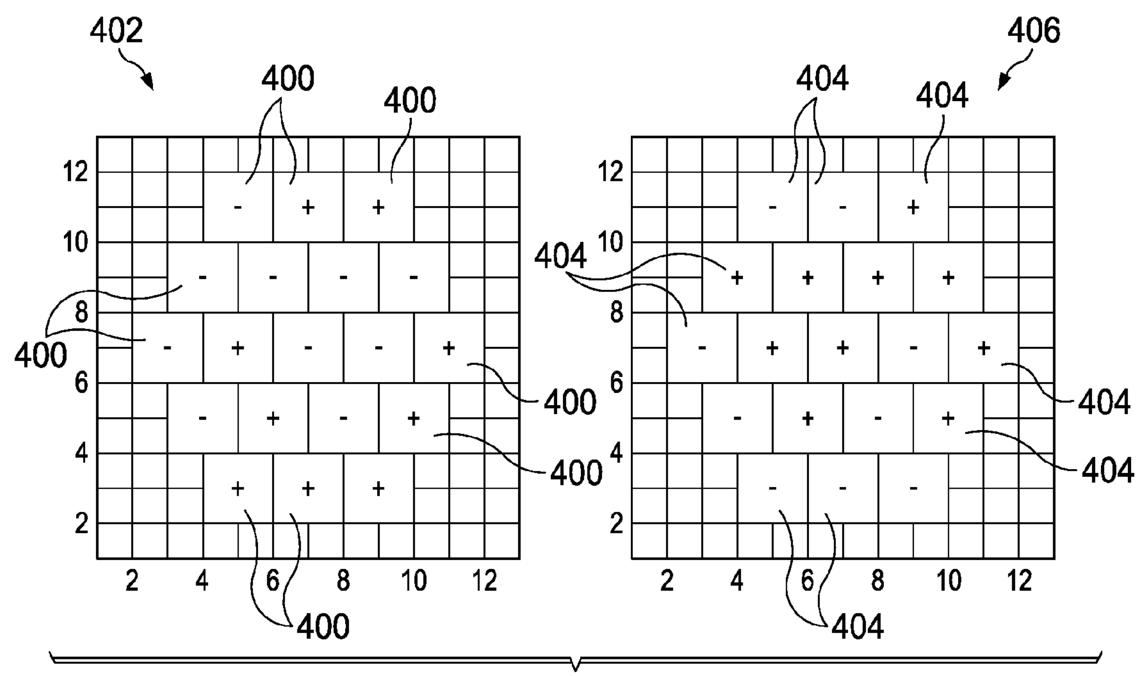
FIG. 4A 700
702
704
706
708
710
712
712a
712b

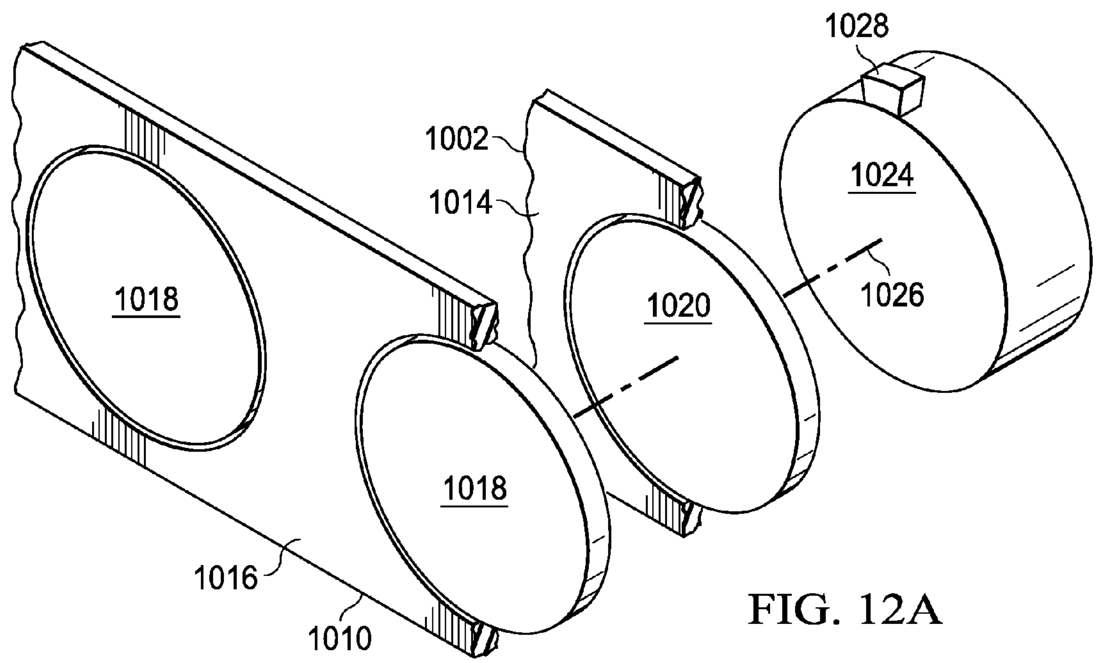
FIG. 12A
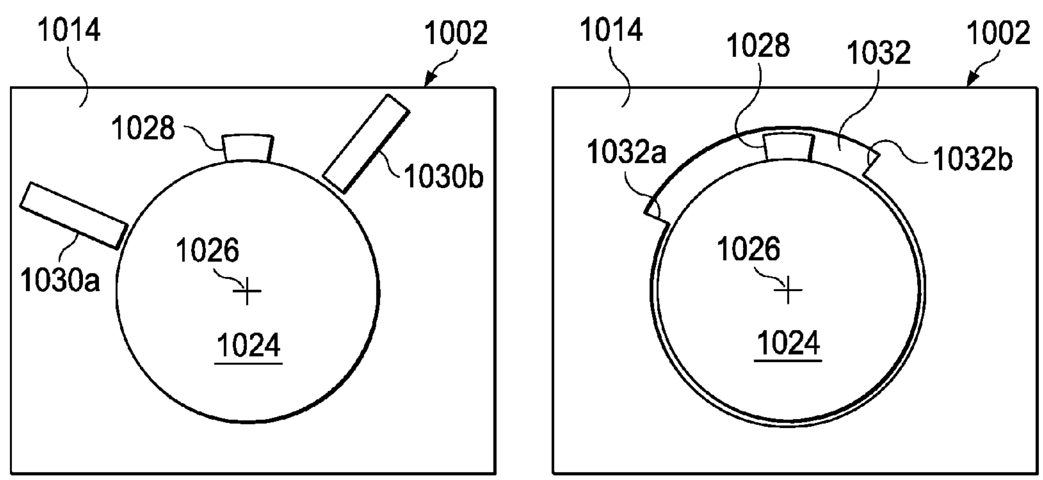
FIG. 12B
FIG. 12C 1302
1306
1308
1310
1312
1300

CORRELATED MAGNETIC MASK AND METHOD FOR USING THE CORRELATED MAGNETIC MASK

CROSS REFERENCE TO RELATED APPLICATIONS

This application is a continuation-in-part application of U.S. patent application Ser. No. 12/476,952 filed on Jun. 2, 2009 and entitled "A Field Emission System and Method", which is a continuation-in-part application of U.S. patent application Ser. No. 12/322,561 filed on Feb. 4, 2009 and entitled "A System and Method for Producing an Electric Pulse", which is a continuation-in-part application of U.S. patent application Ser. No. 12/358,423 filed on Jan. 23, 2009 and entitled "A Field Emission System and Method", which is a continuation-in-part application of U.S. patent application Ser. No. 12/123,718 filed on May 20, 2008 and entitled "A Field Emission System and Method". The contents of these four documents are hereby incorporated herein by reference.

TECHNICAL FIELD

The present invention is related to a mask that uses correlated magnets which enable a person to easily secure and remove the mask to and from their head. Some examples of such a mask include a scuba mask, a welding mask, a fencing mask, a goalie mask, a paint mask, a paintball mask, a catcher's mask, a ski mask, a goalie mask, an oxygen mask, a surgical mask, a face shield, a filter mask, a theatrical mask, a costume mask, a continuous positive airway pressure (CPAP) mask. The present invention is demonstrated using the scuba mask.

DESCRIPTION OF RELATED ART

In the scuba diving field, for example, it would be desirable to provide a person with a scuba mask that the person can easily secure to their head and regulate the length and tension of the strap around their head. In addition, it would be desirable if the person could easily remove the mask from their head. Unfortunately, the traditional scuba masks all employ loops, buckles, clamps, hooks, or other known fastening mechanisms which require a great degree of dexterity on the part of the person to use when they want to secure or remove the scuba mask from their head. Accordingly, there has been a need for a new type of scuba mask which addresses the aforementioned shortcoming and other shortcomings associated with the traditional scuba mask. In addition, there is a need for a similar type of new mask that can be used in other environments like, for example, hospitals, laboratories, construction, and military. These needs and other needs are satisfied by the present invention.

SUMMARY

In one aspect, the present invention provides a mask including a frame that supports at least one lens, where the frame has a first support with a first end of a strap attached thereto, where the strap has a second end which incorporates a first field emission structure, where the frame has a second support which incorporates a second field emission structure, where the second end of the strap is attached to the second support of the frame when the first and second field emission structures are located next to one another and have a certain alignment with respect to one another, where each of the first and second field emission structures include field emission sources having positions and polarities relating to a desired spatial force function that corresponds to a relative alignment of the first and second field emission structures within a field domain. The second end of the strap can be released from the second end of the frame when the first and second field emission structures are turned with respect to one another. The attachment and release of the second end of the strap to and from the second support of the frame is possible because source of each field emission source has a corresponding field emission amplitude and vector direction determined in accordance with the desired spatial force function, wherein a separation distance between the first and second field emission structures and the relative alignment of the first and second field emission structures creates a spatial force in accordance the desired spatial force function. And, the field domain corresponds to first field emissions from the first field emission sources of the first field emission structure interacting with second field emissions from the second field emission sources of the second field emission structure.

In another aspect, the present invention provides a method for using a mask including the steps of: (a) placing the mask on a head of a person, where the mask includes a frame that supports at least one lens, where the frame has a first support with a first end of a strap attached thereto, where the strap has a second end which incorporates a first field emission structure, where the frame has a second support which incorporates a second field emission structure, and (b) pulling the second end of the strap around the head of the person so the first field emission structure interacts with the second field emission structure, where the second end of the strap is attached to the second support of the frame when the first and second field emission structures are located next to one another and have a certain alignment with respect to one another, and where each of the first and second field emission structures include field emission sources having positions and polarities relating to a desired spatial force function that corresponds to a relative alignment of the first and second field emission structures within a field domain. The second end of the strap can be released from the second support of the frame when the first and second field emission structures are turned with respect to one another.

Additional aspects of the invention will be set forth, in part, in the detailed description, figures and any claims which follow, and in part will be derived from the detailed description, or can be learned by practice of the invention. It is to be understood that both the foregoing general description and the following detailed description are exemplary and explanatory only and are not restrictive of the invention as disclosed.

BRIEF DESCRIPTION OF THE DRAWINGS

A more complete understanding of the present invention may be obtained by reference to the following detailed description when taken in conjunction with the accompanying drawings wherein:

FIGS. 12A-12C illustrate several diagrams of an exemplary release mechanism that can be incorporated within the frame of the correlated magnetic scuba mask shown in FIGS. 10A-10C in accordance with an embodiment of the present invention.

DETAILED DESCRIPTION

The present invention includes a mask that uses correlated magnets which enable a person to easily secure and remove the mask to and from their head. The mask utilizes correlated magnetic technology which is a significant improvement over a conventional mask which employs loops, buckles, clamps, hooks, or other known fastening devices so the person can secure and remove the mask to and from their head. This significant improvement over the state-of-art is attributable, in part, to the use of an emerging, revolutionary technology that is called correlated magnetics. This new revolutionary technology called correlated magnetics was first fully described and enabled in the co-assigned U.S. patent application Ser. No. 12/123,718 filed on May 20, 2008 and entitled "A Field Emission System and Method". The contents of this document are hereby incorporated herein by reference. A second generation of a correlated magnetic technology is described and enabled in the co-assigned U.S. patent application Ser. No. 12/358,423 filed on Jan. 23, 2009 and entitled "A Field Emission System and Method". The contents of this document are hereby incorporated herein by reference. A third generation of a correlated magnetic technology is described and enabled in the co-assigned U.S. patent application Ser. No. 12/476,952 filed on Jun. 2, 2009 and entitled "A Field Emission System and Method". The contents of this document are hereby incorporated herein by reference. Another technology known as correlated inductance, which is related to correlated magnetics, has been described and enabled in the co-assigned U.S. patent application Ser. No. 12/322,561 filed on Feb. 4, 2009 and entitled "A System and Method for Producing and Electric Pulse". A brief discussion about correlated magnetics is provided first before a detailed discussion is provided about the correlated magnetic mask of the present invention.

Correlated Magnetics Technology

This section is provided to introduce the reader to basic magnets and the new and revolutionary correlated magnetic technology. This section includes subsections relating to basic magnets, correlated magnets, and correlated electromagnetics. It should be understood that this section is provided to assist the reader with understanding the present invention, and should not be used to limit the scope of the present invention.

A. Magnets

Figure 1:
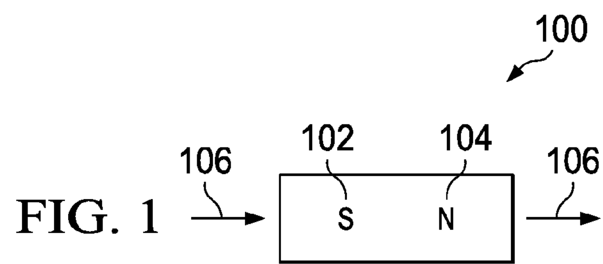
FIGS. 1-9 are various diagrams used to help explain different concepts about correlated magnetic technology which can be utilized in an embodiment of the present invention.

A magnet is a material or object that produces a magnetic field which is a vector field that has a direction and a magnitude (also called strength). Referring to FIG. 1, there is illustrated an exemplary magnet 100 which has a South pole 102 and a North pole 104 and magnetic field vectors 106 that represent the direction and magnitude of the magnet's moment. The magnet's moment is a vector that characterizes the overall magnetic properties of the magnet 100. For a bar magnet, the direction of the magnetic moment points from the South pole 102 to the North pole 104. The North and South poles 104 and 102 are also referred to herein as positive (+) and negative (−) poles, respectively.

Figure 2A:
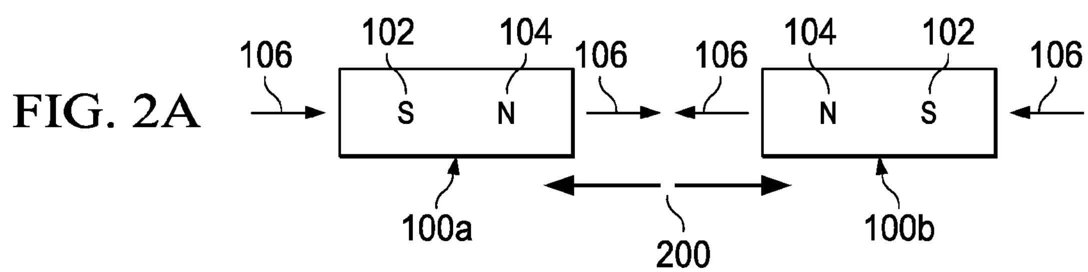
Figure 2B:
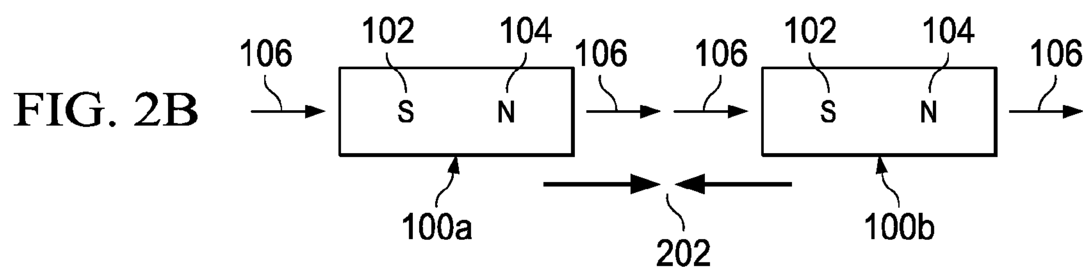
Figure 2C:
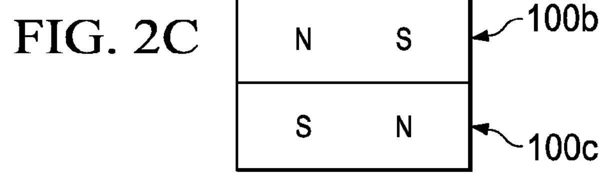

Referring to FIG. 2A, there is a diagram that depicts two magnets 100*a* and 100*b* aligned such that their polarities are opposite in direction resulting in a repelling spatial force 200 which causes the two magnets 100*a* and 100*b* to repel each other. In contrast, FIG. 2B is a diagram that depicts two magnets 100*a* and 100*b* aligned such that their polarities are in the same direction resulting in an attracting spatial force 202 which causes the two magnets 100*a* and 100*b* to attract each other. In FIG. 2B, the magnets 100*a* and 100*b* are shown as being aligned with one another but they can also be partially aligned with one another where they could still "stick" to each other and maintain their positions relative to each other. FIG. 2C is a diagram that illustrates how magnets 100*a*, 100*b* and 100*c* will naturally stack on one another such that their poles alternate.

B. Correlated Magnets

Correlated magnets can be created in a wide variety of ways depending on the particular application as described in the aforementioned U.S. patent application Ser. Nos. 12/123,718, 12/358,432, and 12/476,952 by using a unique combination of magnet arrays (referred to herein as magnetic field emission sources), correlation theory (commonly associated with probability theory and statistics) and coding theory (commonly associated with communication systems). A brief discussion is provided next to explain how these widely diverse technologies are used in a unique and novel way to create correlated magnets.

Basically, correlated magnets are made from a combination of magnetic (or electric) field emission sources which have been configured in accordance with a pre-selected code having desirable correlation properties. Thus, when a magnetic field emission structure is brought into alignment with a complementary, or mirror image, magnetic field emission structure the various magnetic field emission sources will all align causing a peak spatial attraction force to be produced, while the misalignment of the magnetic field emission structures cause the various magnetic field emission sources to substantially cancel each other out in a manner that is a function of the particular code used to design the two magnetic field emission structures. In contrast, when a magnetic field emission structure is brought into alignment with a duplicate magnetic field emission structure then the various magnetic field emission sources all align causing a peak spatial repelling force to be produced, while the misalignment of the magnetic field emission structures causes the various magnetic field emission sources to substantially cancel each other out in a manner that is a function of the particular code used to design the two magnetic field emission structures.

The aforementioned spatial forces (attraction, repelling) have a magnitude that is a function of the relative alignment of two magnetic field emission structures and their corresponding spatial force (or correlation) function, the spacing (or distance) between the two magnetic field emission structures, and the magnetic field strengths and polarities of the various sources making up the two magnetic field emission structures. The spatial force functions can be used to achieve precision alignment and precision positioning not possible with basic magnets. Moreover, the spatial force functions can enable the precise control of magnetic fields and associated spatial forces thereby enabling new forms of attachment devices for attaching objects with precise alignment and new systems and methods for controlling precision movement of objects. An additional unique characteristic associated with correlated magnets relates to the situation where the various magnetic field sources making-up two magnetic field emission structures can effectively cancel out each other when they are brought out of alignment which is described herein as a release force. This release force is a direct result of the particular correlation coding used to configure the magnetic field emission structures.

A person skilled in the art of coding theory will recognize that there are many different types of codes that have different correlation properties which have been used in communications for channelization purposes, energy spreading, modulation, and other purposes. Many of the basic characteristics of such codes make them applicable for use in producing the magnetic field emission structures described herein. For example, Barker codes are known for their autocorrelation properties and can be used to help configure correlated magnets. Although, a Barker code is used in an example below with respect to FIGS. 3A-3B, other forms of codes which may or may not be well known in the art are also applicable to correlated magnets because of their autocorrelation, cross-correlation, or other properties including, for example, Gold codes, Kasami sequences, hyperbolic congruential codes, quadratic congruential codes, linear congruential codes, Welch-Costas array codes, Golomb-Costas array codes, pseudorandom codes, chaotic codes, Optimal Golomb Ruler codes, deterministic codes, designed codes, one dimensional codes, two dimensional codes, three dimensional codes, or four dimensional codes, combinations thereof, and so forth.

Figure 3A:
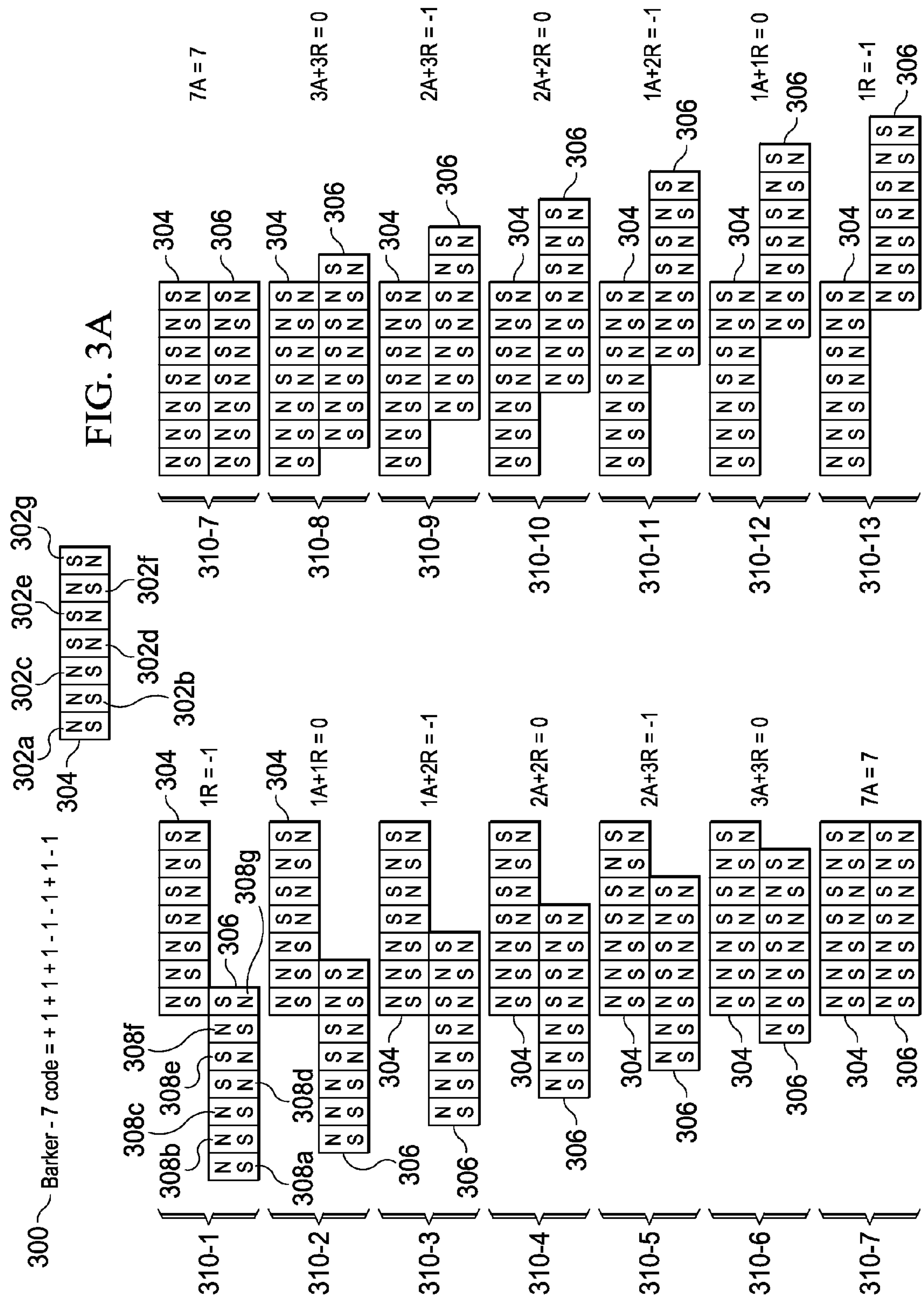

Referring to FIG. 3A, there are diagrams used to explain how a Barker length 7 code 300 can be used to determine polarities and positions of magnets 302*a*, 302*b* . . . 302*g* making up a first magnetic field emission structure 304. Each magnet 302*a*, 302*b* . . . 302*g* has the same or substantially the same magnetic field strength (or amplitude), which for the sake of this example is provided as a unit of 1 (where A=Attract, R=Repel, A=−R, A=1, R=−1). A second magnetic field emission structure 306 (including magnets 308*a*, 308*b* . . . 308*g*) that is identical to the first magnetic field emission structure 304 is shown in 13 different alignments 310-1 through 310-13 relative to the first magnetic field emission structure 304. For each relative alignment, the number of magnets that repel plus the number of magnets that attract is calculated, where each alignment has a spatial force in accordance with a spatial force function based upon the correlation function and magnetic field strengths of the magnets 302*a*, 302*b* . . . 302*g* and 308*a*, 308*b* . . . 308*g*. With the specific Barker code used, the spatial force varies from −1 to 7, where the peak occurs when the two magnetic field emission structures 304 and 306 are aligned which occurs when their respective codes are aligned. The off peak spatial force, referred to as a side lobe force, varies from 0 to −1. As such, the spatial force function causes the magnetic field emission structures 304 and 306 to generally repel each other unless they are aligned such that each of their magnets are correlated with a complementary magnet (i.e., a magnet's South pole aligns with another magnet's North pole, or vice versa). In other words, the two magnetic field emission structures 304 and 306 substantially correlate with one another when they are aligned to substantially mirror each other.

In FIG. 3B, there is a plot that depicts the spatial force function of the two magnetic field emission structures 304 and 306 which results from the binary autocorrelation function of the Barker length 7 code 300, where the values at each alignment position 1 through 13 correspond to the spatial force values that were calculated for the thirteen alignment positions 310-1 through 310-13 between the two magnetic field emission structures 304 and 306 depicted in FIG. 3A. As the true autocorrelation function for correlated magnet field structures is repulsive, and most of the uses envisioned will have attractive correlation peaks, the usage of the term 'autocorrelation' herein will refer to complementary correlation unless otherwise stated. That is, the interacting faces of two such correlated magnetic field emission structures 304 and 306 will be complementary to (i.e., mirror images of) each other. This complementary autocorrelation relationship can be seen in FIG. 3A where the bottom face of the first magnetic field emission structure 304 having the pattern 'S S S N N S N' is shown interacting with the top face of the second magnetic field emission structure 306 having the pattern 'N N N S S N S', which is the mirror image (pattern) of the bottom face of the first magnetic field emission structure 304.

Figure 4B:
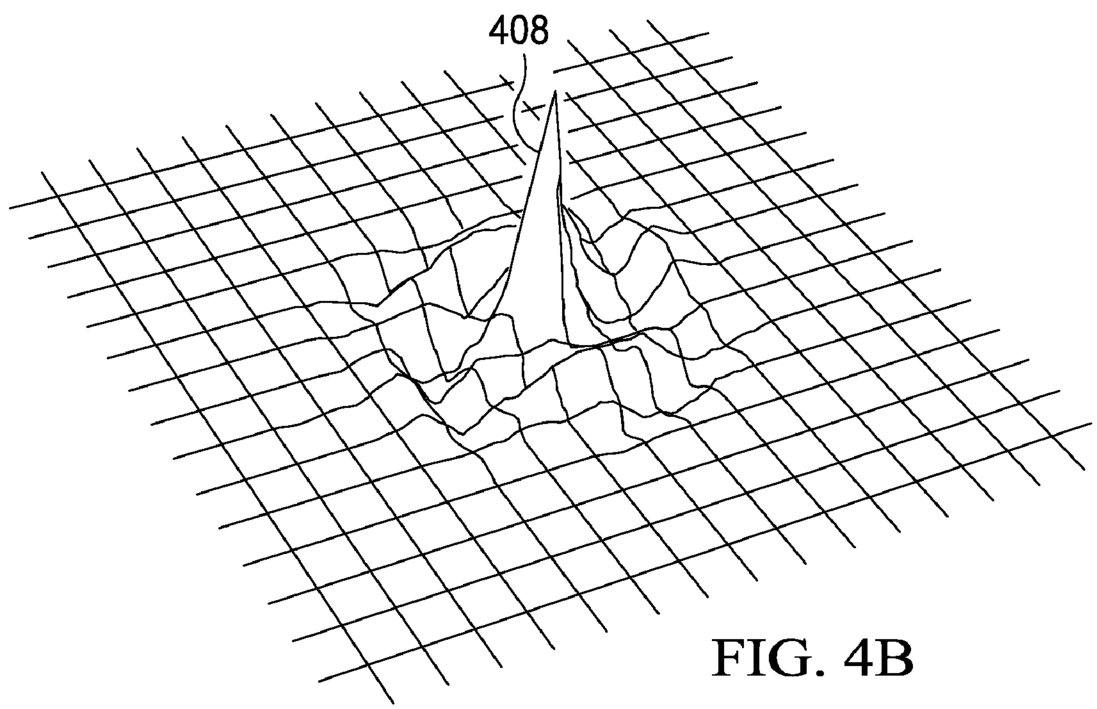
Figure 4C:
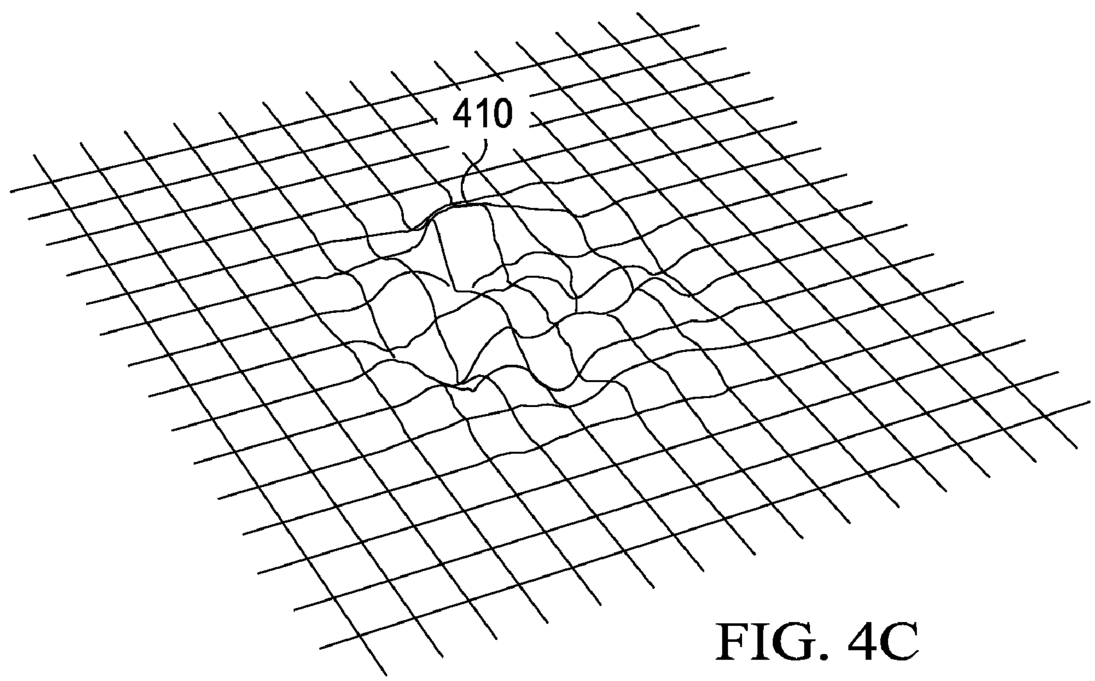

Referring to FIG. 4A, there is a diagram of an array of 19 magnets 400 positioned in accordance with an exemplary code to produce an exemplary magnetic field emission structure 402 and another array of 19 magnets 404 which is used to produce a mirror image magnetic field emission structure 406. In this example, the exemplary code was intended to produce the first magnetic field emission structure 402 to have a first stronger lock when aligned with its mirror image magnetic field emission structure 406 and a second weaker lock when it is rotated 90° relative to its mirror image magnetic field emission structure 406. FIG. 4B depicts a spatial force function 408 of the magnetic field emission structure 402 interacting with its mirror image magnetic field emission structure 406 to produce the first stronger lock. As can be seen, the spatial force function 408 has a peak which occurs when the two magnetic field emission structures 402 and 406 are substantially aligned. FIG. 4C depicts a spatial force function 410 of the magnetic field emission structure 402 interacting with its mirror magnetic field emission structure 406 after being rotated 90°. As can be seen, the spatial force function 410 has a smaller peak which occurs when the two magnetic field emission structures 402 and 406 are substantially aligned but one structure is rotated 900. If the two magnetic field emission structures 402 and 406 are in other positions then they could be easily separated.

Figure 5:
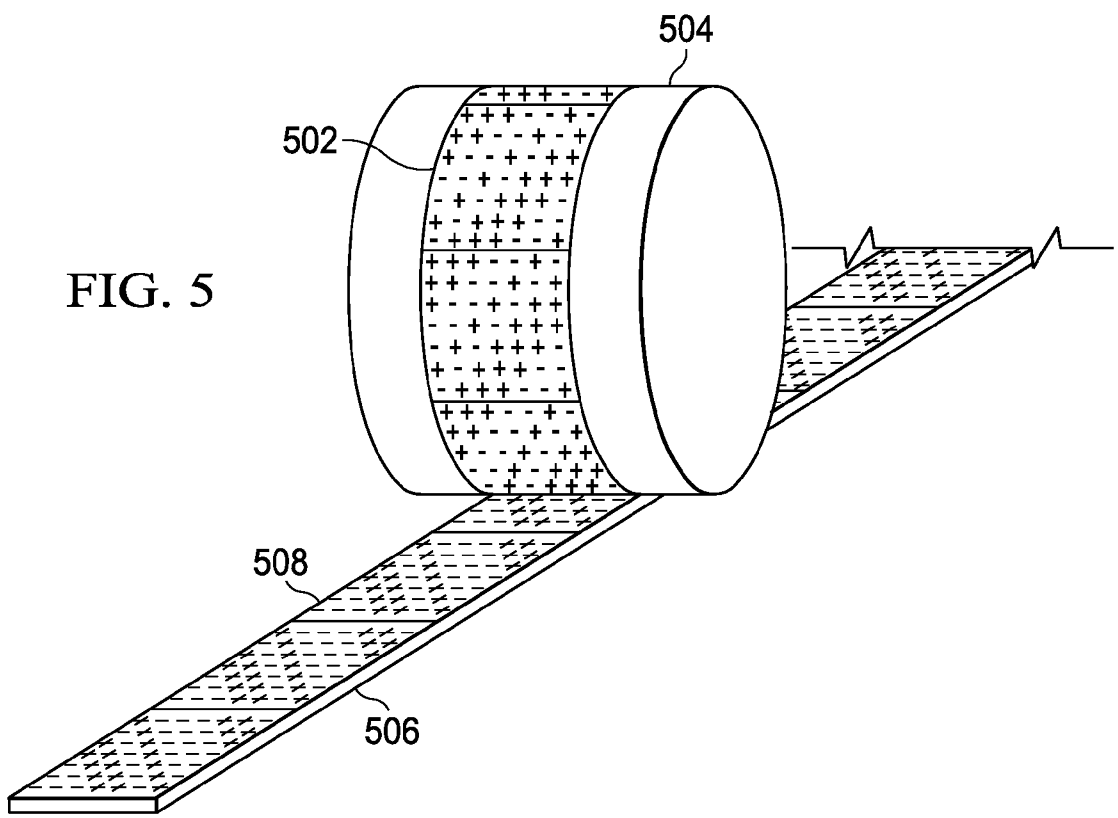

Referring to FIG. 5, there is a diagram depicting a correlating magnet surface 502 being wrapped back on itself on a cylinder 504 (or disc 504, wheel 504) and a conveyor belt/tracked structure 506 having located thereon a mirror image correlating magnet surface 508. In this case, the cylinder 504 can be turned clockwise or counter-clockwise by some force so as to roll along the conveyor belt/tracked structure 506. The fixed magnetic field emission structures 502 and 508 provide a traction and gripping (i.e., holding) force as the cylinder 504 is turned by some other mechanism (e.g., a motor). The gripping force would remain substantially constant as the cylinder 504 moved down the conveyor belt/tracked structure 506 independent of friction or gravity and could therefore be used to move an object about a track that moved up a wall, across a ceiling, or in any other desired direction within the limits of the gravitational force (as a function of the weight of the object) overcoming the spatial force of the aligning magnetic field emission structures 502 and 508. If desired, this cylinder 504 (or other rotary devices) can also be operated against other rotary correlating surfaces to provide a gear-like operation. Since the hold-down force equals the traction force, these gears can be loosely connected and still give positive, non-slipping rotational accuracy. Plus, the magnetic field emission structures 502 and 508 can have surfaces which are perfectly smooth and still provide positive, non-slip traction. In contrast to legacy friction-based wheels, the traction force provided by the magnetic field emission structures 502 and 508 is largely independent of the friction forces between the traction wheel and the traction surface and can be employed with low friction surfaces. Devices moving about based on magnetic traction can be operated independently of gravity for example in weightless conditions including space, underwater, vertical surfaces and even upside down.

Figure 6:
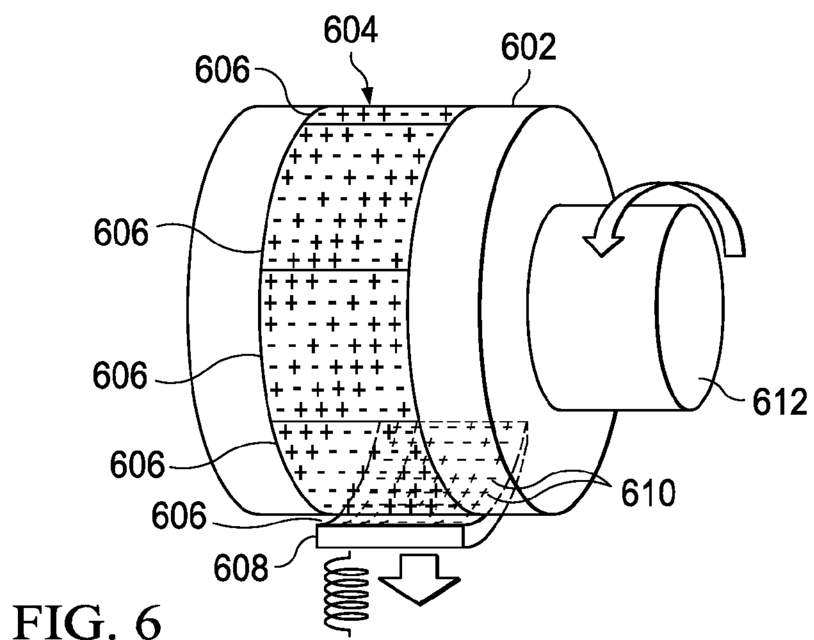

Referring to FIG. 6, there is a diagram depicting an exemplary cylinder 602 having wrapped thereon a first magnetic field emission structure 604 with a code pattern 606 that is repeated six times around the outside of the cylinder 602. Beneath the cylinder 602 is an object 608 having a curved surface with a slightly larger curvature than the cylinder 602 and having a second magnetic field emission structure 610 that is also coded using the code pattern 606. Assume, the cylinder 602 is turned at a rotational rate of 1 rotation per second by shaft 612. Thus, as the cylinder 602 turns, six times a second the first magnetic field emission structure 604 on the cylinder 602 aligns with the second magnetic field emission structure 610 on the object 608 causing the object 608 to be repelled (i.e., moved downward) by the peak spatial force function of the two magnetic field emission structures 604 and 610. Similarly, had the second magnetic field emission structure 610 been coded using a code pattern that mirrored code pattern 606, then 6 times a second the first magnetic field emission structure 604 of the cylinder 602 would align with the second magnetic field emission structure 610 of the object 608 causing the object 608 to be attracted (i.e., moved upward) by the peak spatial force function of the two magnetic field emission structures 604 and 610. Thus, the movement of the cylinder 602 and the corresponding first magnetic field emission structure 604 can be used to control the movement of the object 608 having its corresponding second magnetic field emission structure 610. One skilled in the art will recognize that the cylinder 602 may be connected to a shaft 612 which may be turned as a result of wind turning a windmill, a water wheel or turbine, ocean wave movement, and other methods whereby movement of the object 608 can result from some source of energy scavenging. As such, correlated magnets enables the spatial forces between objects to be precisely controlled in accordance with their movement and also enables the movement of objects to be precisely controlled in accordance with such spatial forces.

In the above examples, the correlated magnets 304, 306, 402, 406, 502, 508, 604 and 610 overcome the normal 'magnet orientation' behavior with the aid of a holding mechanism such as an adhesive, a screw, a bolt & nut, etc . . . . In other cases, magnets of the same magnetic field emission structure could be sparsely separated from other magnets (e.g., in a sparse array) such that the magnetic forces of the individual magnets do not substantially interact, in which case the polarity of individual magnets can be varied in accordance with a code without requiring a holding mechanism to prevent magnetic forces from 'flipping' a magnet. However, magnets are typically close enough to one another such that their magnetic forces would substantially interact to cause at least one of them to 'flip' so that their moment vectors align but these magnets can be made to remain in a desired orientation by use of a holding mechanism such as an adhesive, a screw, a bolt & nut, etc . . . . As such, correlated magnets often utilize some sort of holding mechanism to form different magnetic field emission structures which can be used in a wide-variety of applications like, for example, a turning mechanism, a tool insertion slot, alignment marks, a latch mechanism, a pivot mechanism, a swivel mechanism, a lever, a drill head assembly, a hole cutting tool assembly, a machine press tool, a gripping apparatus, a slip ring mechanism, and a structural assembly.

C. Correlated Electromagnetics

Correlated magnets can entail the use of electromagnets which is a type of magnet in which the magnetic field is produced by the flow of an electric current. The polarity of the magnetic field is determined by the direction of the electric current and the magnetic field disappears when the current ceases. Following are a couple of examples in which arrays of electromagnets are used to produce a first magnetic field emission structure that is moved over time relative to a second magnetic field emission structure which is associated with an object thereby causing the object to move.

Figure 7:
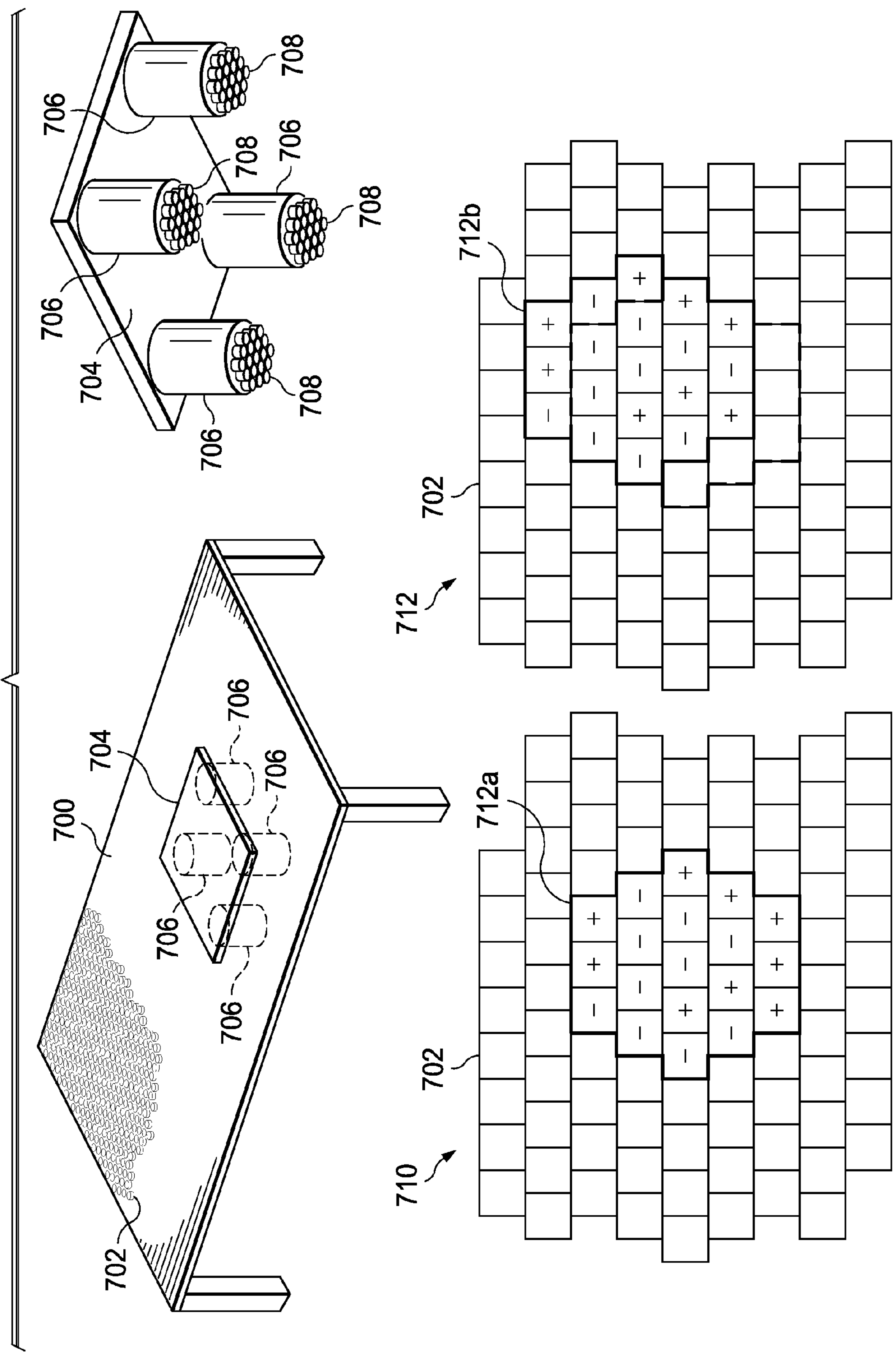

Referring to FIG. 7, there are several diagrams used to explain a 2-D correlated electromagnetics example in which there is a table 700 having a two-dimensional electromagnetic array 702 (first magnetic field emission structure 702) beneath its surface and a movement platform 704 having at least one table contact member 706. In this example, the movement platform 704 is shown having four table contact members 706 each having a magnetic field emission structure 708 (second magnetic field emission structures 708) that would be attracted by the electromagnetic array 702. Computerized control of the states of individual electromagnets of the electromagnet array 702 determines whether they are on or off and determines their polarity. A first example 710 depicts states of the electromagnetic array 702 configured to cause one of the table contact members 706 to attract to a subset 712*a* of the electromagnets within the magnetic field emission structure 702. A second example 712 depicts different states of the electromagnetic array 702 configured to cause the one table contact member 706 to be attracted (i.e., move) to a different subset 712*b* of the electromagnets within the field emission structure 702. Per the two examples, one skilled in the art can recognize that the table contact member(s) 706 can be moved about table 700 by varying the states of the electromagnets of the electromagnetic array 702.

Figure 8:
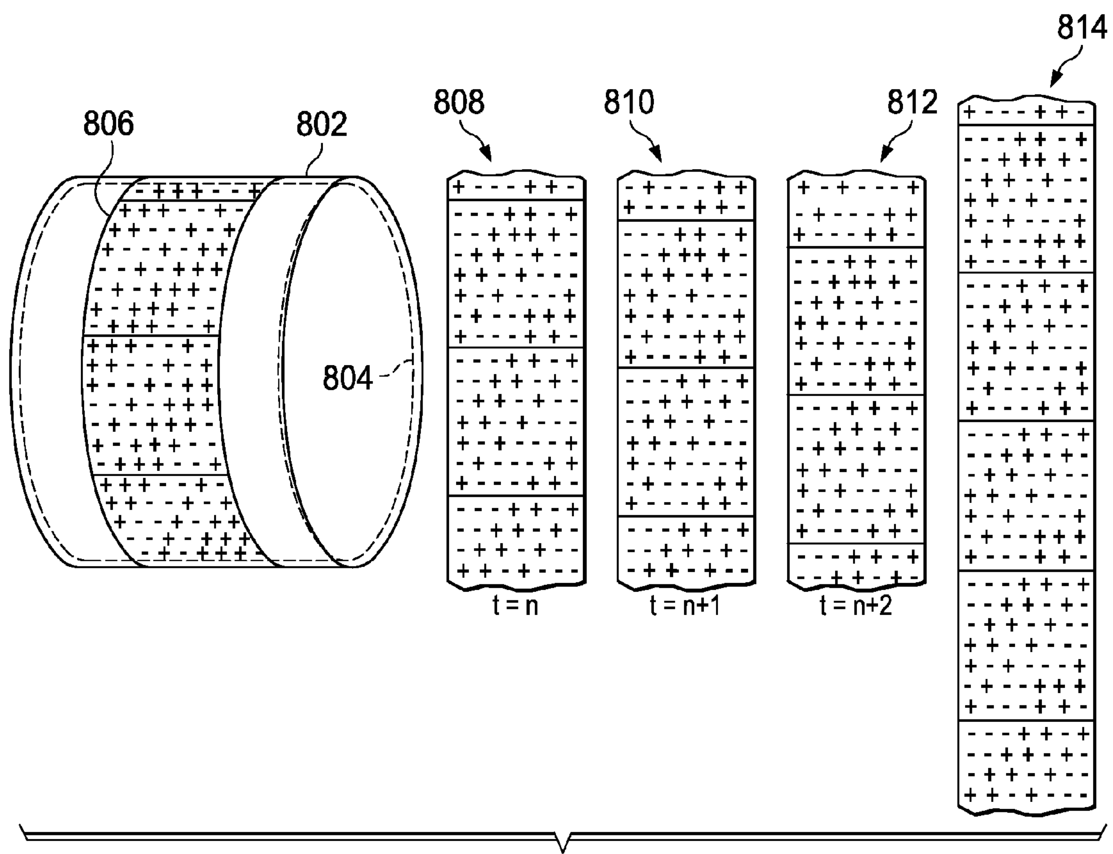

Referring to FIG. 8, there are several diagrams used to explain a 3-D correlated electromagnetics example where there is a first cylinder 802 which is slightly larger than a second cylinder 804 that is contained inside the first cylinder 802. A magnetic field emission structure 806 is placed around the first cylinder 802 (or optionally around the second cylinder 804). An array of electromagnets (not shown) is associated with the second cylinder 804 (or optionally the first cylinder 802) and their states are controlled to create a moving mirror image magnetic field emission structure to which the magnetic field emission structure 806 is attracted so as to cause the first cylinder 802 (or optionally the second cylinder 804) to rotate relative to the second cylinder 804 (or optionally the first cylinder 802). The magnetic field emission structures 808, 810, and 812 produced by the electromagnetic array on the second cylinder 804 at time t=n, t=n+1, and t=n+2, show a pattern mirroring that of the magnetic field emission structure 806 around the first cylinder 802. The pattern is shown moving downward in time so as to cause the first cylinder 802 to rotate counterclockwise. As such, the speed and direction of movement of the first cylinder 802 (or the second cylinder 804) can be controlled via state changes of the electromagnets making up the electromagnetic array. Also depicted in FIG. 8 there is an electromagnetic array 814 that corresponds to a track that can be placed on a surface such that a moving mirror image magnetic field emission structure can be used to move the first cylinder 802 backward or forward on the track using the same code shift approach shown with magnetic field emission structures 808, 810, and 812 (compare to FIG. 5).

Figure 9:
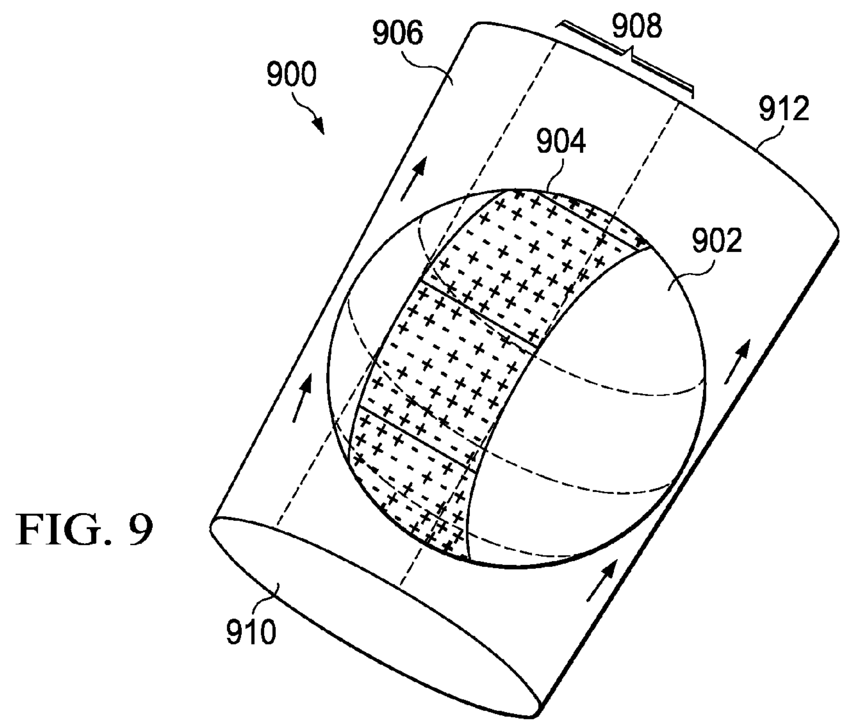

Referring to FIG. 9, there is illustrated an exemplary valve mechanism 900 based upon a sphere 902 (having a magnetic field emission structure 904 wrapped thereon) which is located in a cylinder 906 (having an electromagnetic field emission structure 908 located thereon). In this example, the electromagnetic field emission structure 908 can be varied to move the sphere 902 upward or downward in the cylinder 906 which has a first opening 910 with a circumference less than or equal to that of the sphere 902 and a second opening 912 having a circumference greater than the sphere 902. This configuration is desirable since one can control the movement of the sphere 902 within the cylinder 906 to control the flow rate of a gas or liquid through the valve mechanism 900. Similarly, the valve mechanism 900 can be used as a pressure control valve. Furthermore, the ability to move an object within another object having a decreasing size enables various types of sealing mechanisms that can be used for the sealing of windows, refrigerators, freezers, food storage containers, boat hatches, submarine hatches, etc., where the amount of sealing force can be precisely controlled. One skilled in the art will recognize that many different types of seal mechanisms that include gaskets, o-rings, and the like can be employed with the use of the correlated magnets. Plus, one skilled in the art will recognize that the magnetic field emission structures can have an array of sources including, for example, a permanent magnet, an electromagnet, an electret, a magnetized ferromagnetic material, a portion of a magnetized ferromagnetic material, a soft magnetic material, or a superconductive magnetic material, some combination thereof, and so forth.

Correlated Magnetic Mask

Referring to FIGS. 10-13, there are disclosed two exemplary correlated magnetic masks 1000 and 1300 and methods for using the two exemplary correlated magnetic masks 1000 and 1300 in accordance with different embodiments of the present invention. Although the two exemplary masks 1000 and 1300 of the present invention are described as being configured like a scuba mask, it should be understood that a similar correlated magnetic mask can be configured for a wide-variety of applications including, for example, a medical mask, a laboratory mask, a welding mask, a fencing mask, a goalie mask, a paint mask, a paintball mask, a catcher's mask, a ski mask, a goalie mask, an oxygen mask, a surgical mask, a face shield, a filter mask, a theatrical mask, a costume mask, a continuous positive airway pressure (CPAP) mask, an industrial mask, and a military mask (gas mask). Accordingly, the correlated magnetic mask 1000 or 1300 and methods for using the correlated magnetic mask 1000 or 1300 should not be construed in a limited manner.

Figure 10A:
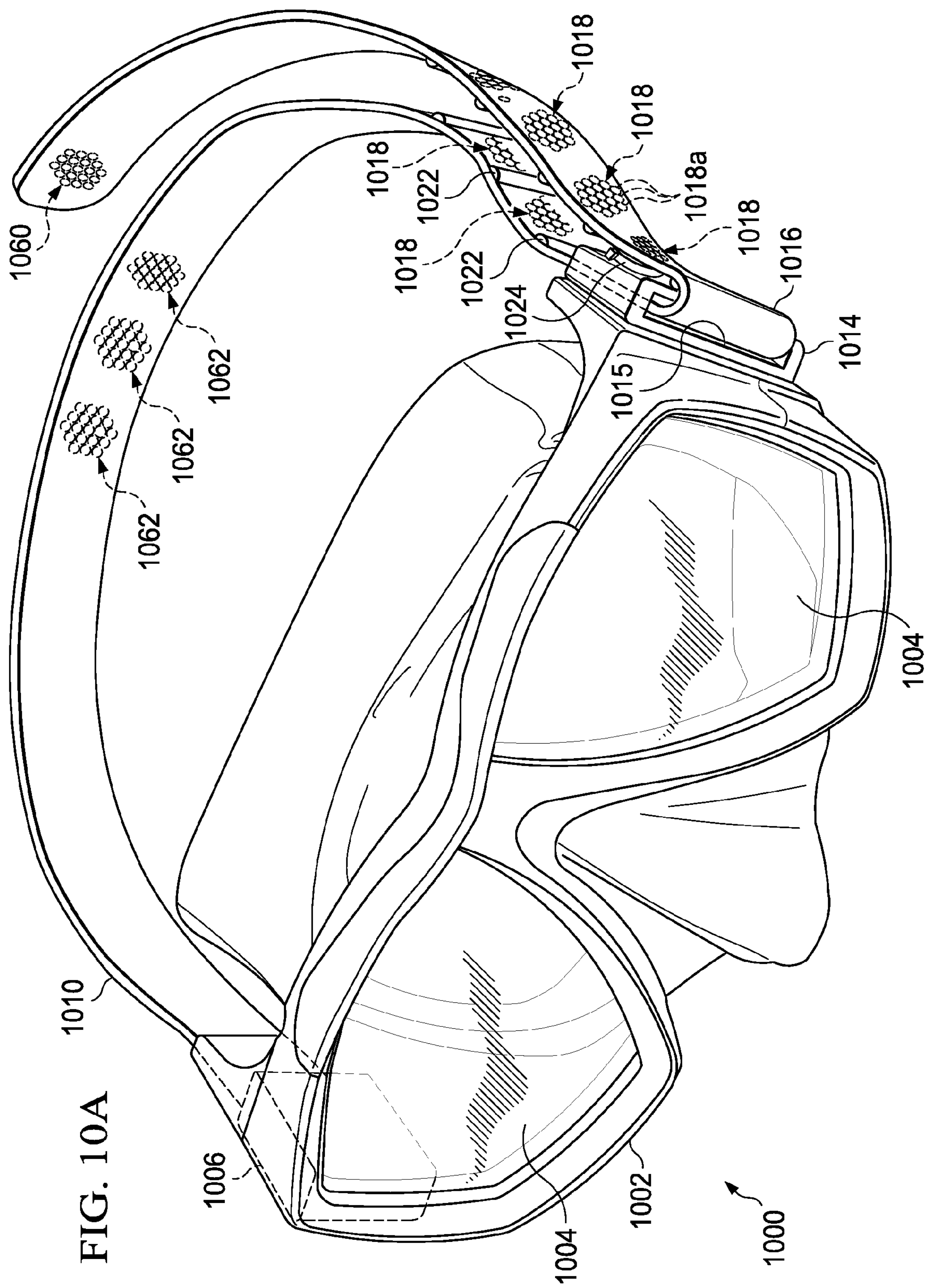
FIGS. 10A-10C are different diagrams of an exemplary correlated magnetic scuba mask in accordance with an embodiment of the present invention.
Figure 10B:
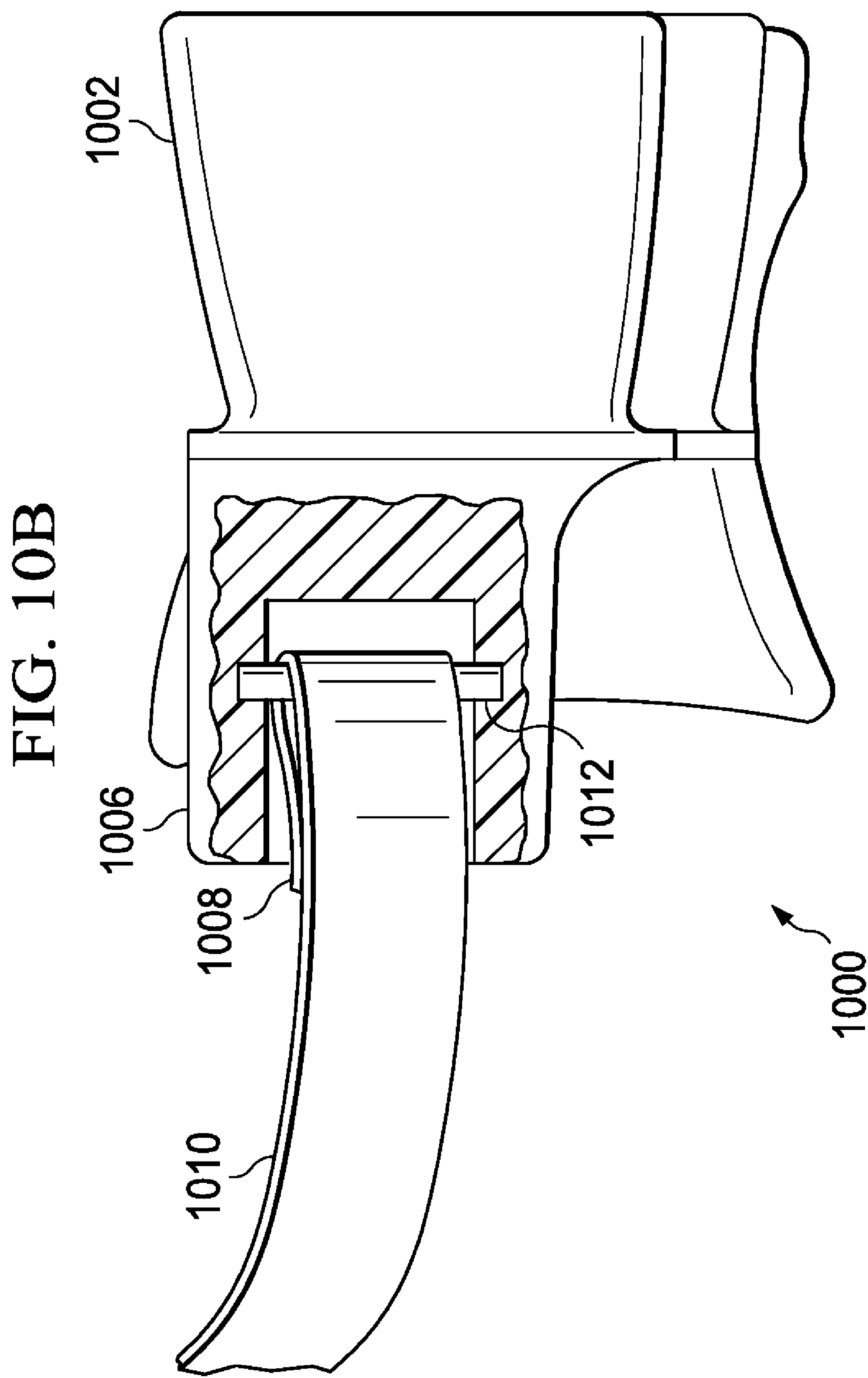
Figure 10C:
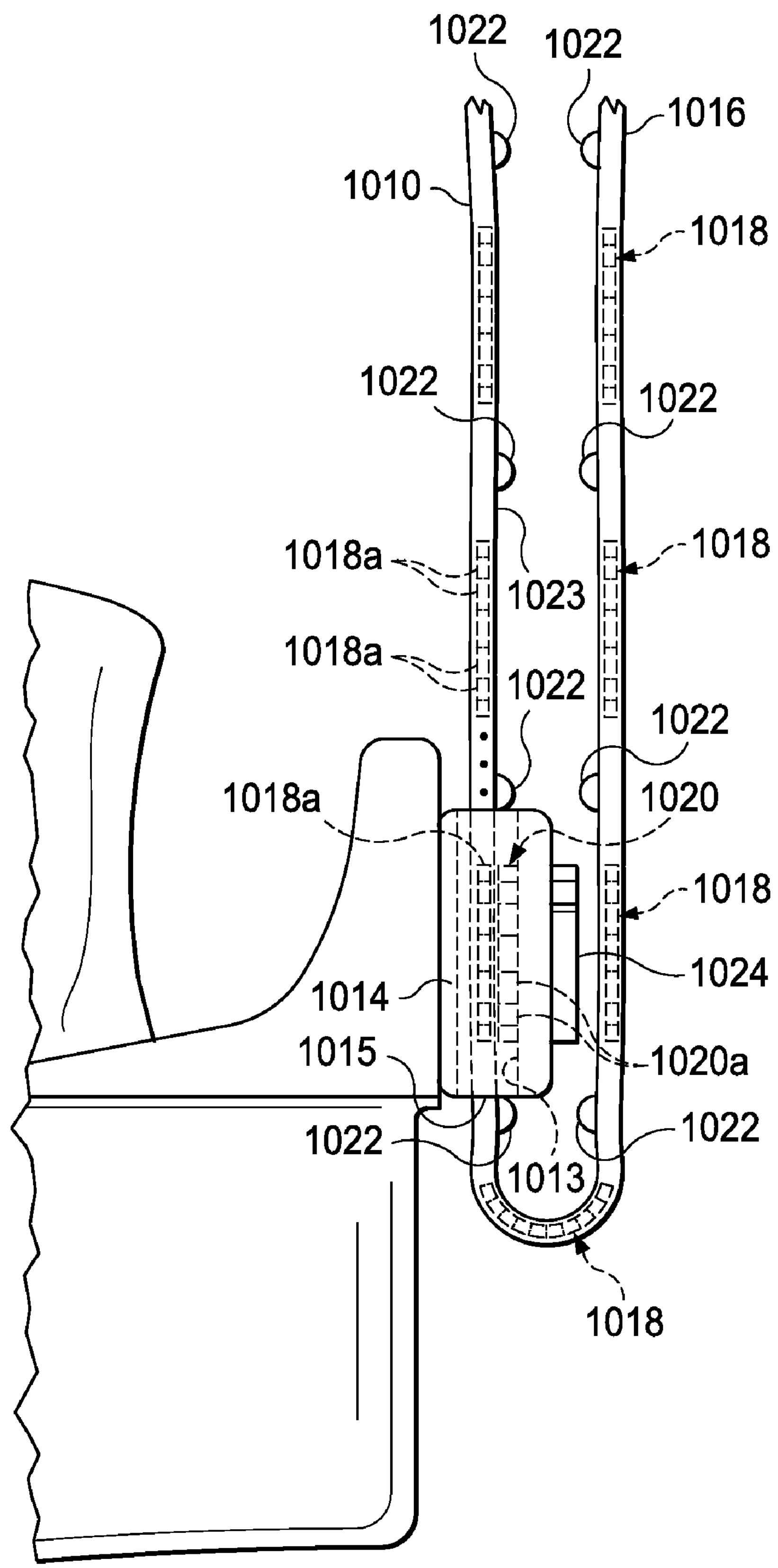

Referring to FIGS. 10A-10C, there are several diagrams of an exemplary correlated magnetic mask 1000 in accordance with an embodiment of the present invention. The correlated magnetic scuba mask 1000 (snorkel mask 1000) includes a frame 1002 which supports one or more transparent lenses 1004 (two shown). The frame 1002 has a first support 1006 at which there is attached thereto one end 1008 of a strap 1010. For instance, the first support 1006 may have a pin 1012 around which is wrapped the first end 1008 of the strap 1010 (see FIG. 10B). The frame 1002 also has a second support 1014 at which a second end 1016 of the strap 1010 can be securely attached thereto or removed therefrom with the aid of correlated magnetic technology (see FIG. 10C).

The strap 1010 has attached thereto (incorporated therein) a series of first magnetic field emission structures 1018 that are located next to one another along a length of the second end 1016 of the strap 1010. The second support 1014 has attached thereto (incorporated therein) a second magnetic field emission structure 1020 which is exposed to or located within an inner portion 1013 of the second support 1014. The first and second magnetic field emissions structures 1018 and 1020 both have the same code but are a mirror image of one another (see FIGS. 4 and 11). In one embodiment, the strap 1010 has a series of first magnetic field emission structures 1018 anyone of which can interface with and attach to the second magnetic field emission structure 1020 incorporated within the second support 1014 of the frame 1002 such that a person can easily secure the mask 1000 to their head and regulate the length and tension of the strap 1010 around their head. In particular, the second end 1016 of the strap 1010 can be pulled through a hole 1015 in the second support 1014 and attached to the inner portion 1013 of the second support 1014 on the frame 1002 when a selected first magnetic field emission structure 1018 and the second magnetic field emission structure 1020 are located next to one another and have a certain alignment with respect to one another (see FIG. 11). If desired, the strap 1010 may have transversal ribs 1022 (or other positioning features) extending from one side 1023 thereof which are located between each of the first magnetic field emission structures 1018 where the transversal ribs 1022 can be used to help position the selected first magnetic field emission structure 1018 next to the second magnetic field emission structure 1020.

The person can easily remove the mask 1000 from their head by separating the attached first and second magnetic field emission structures 1018 and 1020. In particular, the strap 1010 can be released from the second support 1014 of the frame 1002 when the selected first magnetic field emission structure 1018 and the second magnetic field emission structure 1020 are turned or misaligned with respect to one another (see FIG. 11). If desired, a release mechanism 1024 can be used to turn the second magnetic field emission structure 1020 with respect to the first magnetic field emission structure 1018 so as to release or attach the strap 1010 from or to the second support 1014 of the frame 1002 (see FIG. 12).

The attachment and de-attachment of the first and second magnetic field emission structures 1018 and 1020 is possible because the first and second magnetic field emission structures 1018 and 1020 each include an array of field emission sources 1018*a* and 1020*a* (e.g., an array of magnets 1018*a* and 1020*a*) each having positions and polarities relating to a desired spatial force function that corresponds to a relative alignment of the first and second magnetic field emission structures 1018 and 1020 within a field domain (see discussion about correlated magnet technology). It should be noted that the first and second field emission structures 1018 and 1020 (and other pairs of field emission structures) depicted in FIGS. 10A-10C and in other drawings associated with exemplary correlated magnetic masks 1000 and 1300 are themselves exemplary. Generally, the field emission structures 1018 and 1020 (and other pairs of field emission structures) could have many different configurations and could be many different types of permanent magnets, electromagnets, and/or electro-permanent magnets where their size, shape, source strengths, coding, and other characteristics can be tailored to meet different requirements. An example of how the second end 1016 of the strap 1010 can be attached (secured) to or removed from the second support 1014 of the frame 1002 with the aid of an optional release mechanism 1024 is discussed in detail below with respect to FIGS. 11A-11I.

If desired, the strap 1010 can have attached thereto (or incorporated therein) a third magnetic field emission structure 1060 at the second end 1016 and at another portion thereof one or more mirror image fourth magnetic field emission structures 1062 can be attached thereto (or incorporated therein). The third magnetic field emission structure 1060 can be attached to one of the fourth magnetic field emission structures 1062 so that the second end 1016 of the strap 1010 does not hang loose when the first and second magnetic field emission structures 1018 and 1020 are attached to one another. The third and fourth magnetic field emission structures 1060 and 1062 may be different than and not interact with the first and second magnetic field emission structures 1018 and 1020 but they would function in a similar manner.

Figure 11A:
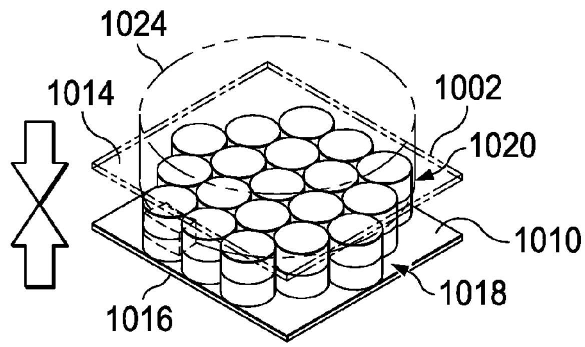
FIGS. 11A-11I are several diagrams that illustrate a portion of the scuba mask which are used to show how an exemplary first magnetic field emission structure (attached to a strap) and its mirror image second magnetic field emission structure (attached to a support on the frame) can be aligned or misaligned relative to each other to enable a person to secure and remove the scuba mask to and from their head in accordance with an embodiment of the present invention.
Figure 11D:
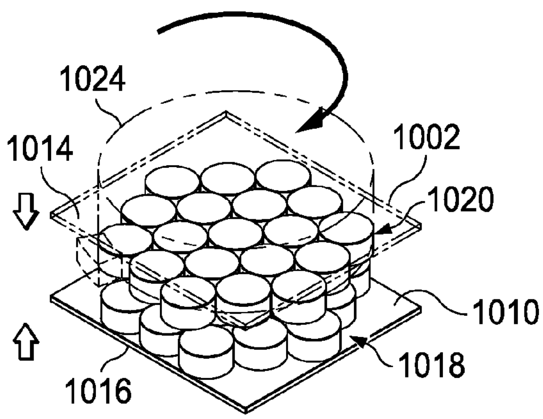
Figure 11B:
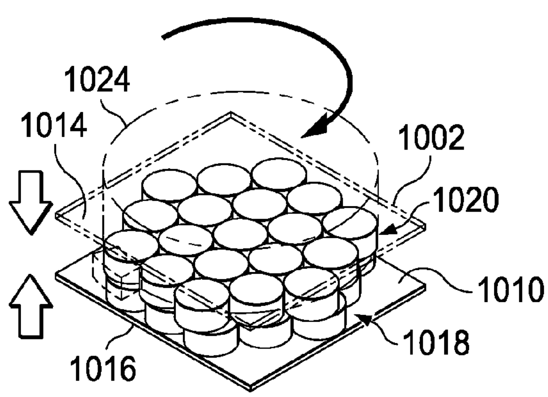
Figure 11E:
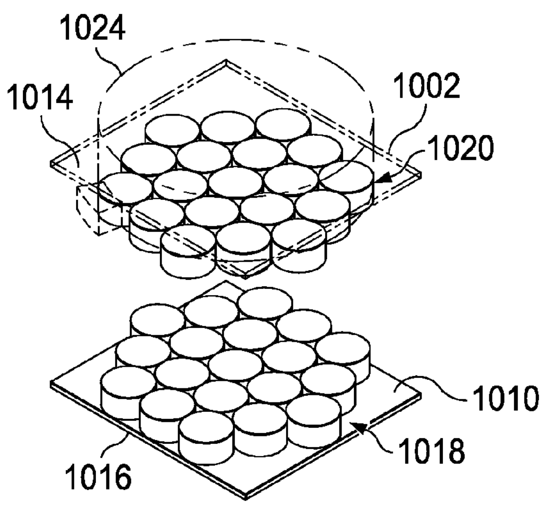
Figure 11C:
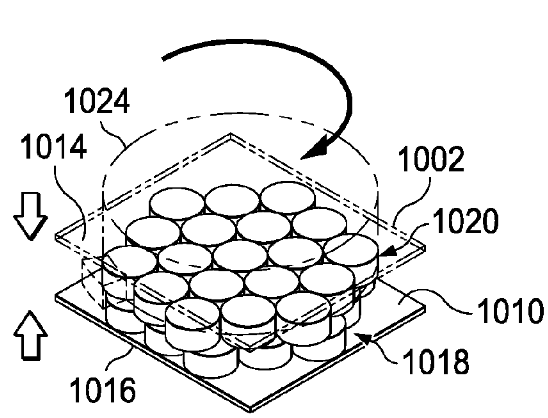
Figure 11F:
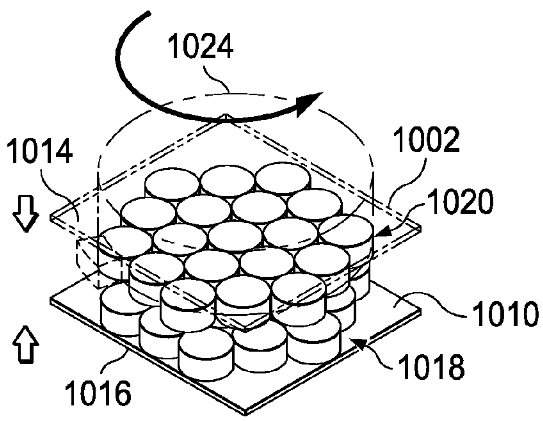
Figure 11G:
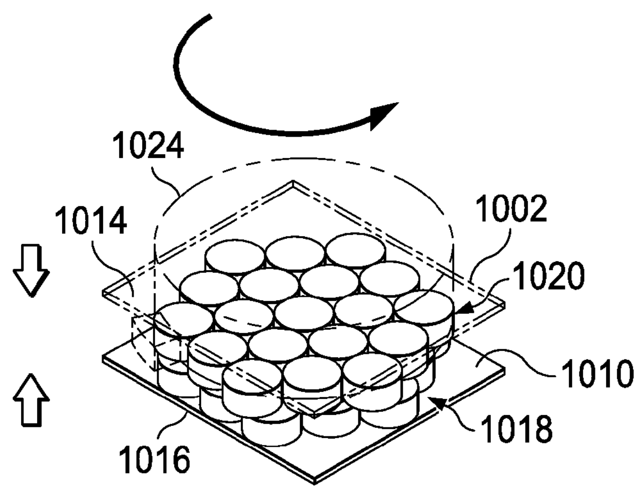
Figure 11H:
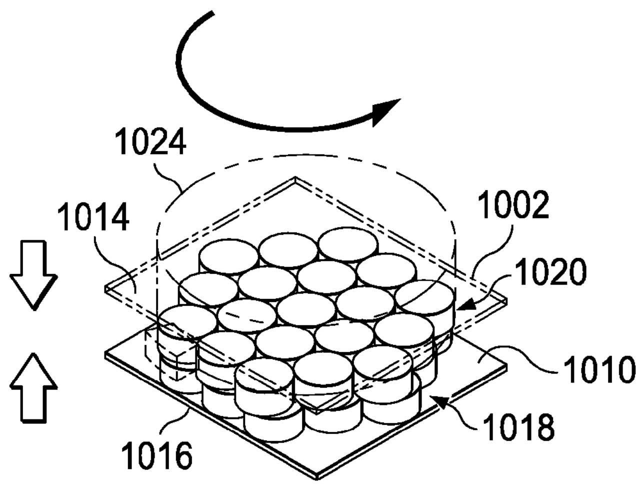
Figure 11I:
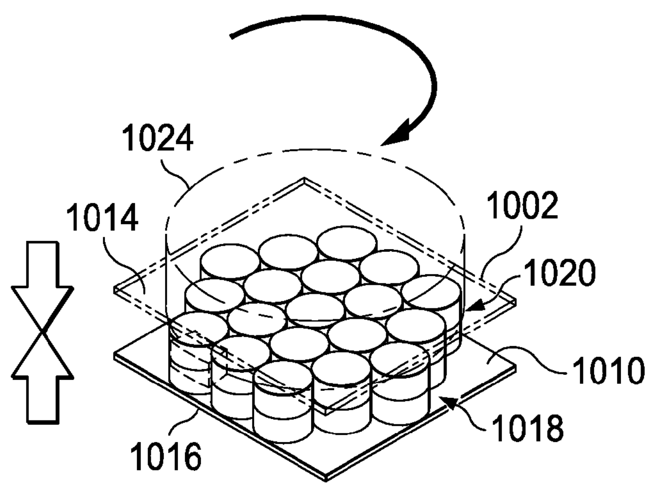

Referring to FIGS. 11A-11I, there is depicted an exemplary selected first magnetic field emission structure 1018 (attached to the second end 1016 of the strap 1010) and its mirror image second magnetic field emission structure 1020 (attached to the second support 1014 of the frame 1002) and the resulting spatial forces produced in accordance with their various alignments as they are twisted relative to each other which enables one to secure or remove the second end 1016 of the strap 1010 to or from the second support 1014 of the frame 1002. In FIG. 11A, the first magnetic field emission structure 1018 and the mirror image second magnetic field emission structure 1020 (attached to the release mechanism 1024) are aligned producing a peak spatial force. In FIG. 11B, the mirror image second magnetic field emission structure 1020 is rotated by the release mechanism 1024 clockwise slightly relative to the first magnetic field emission structure 1018 and the attractive force reduces significantly. In this example, the second support 1014 itself is not rotated but the release mechanism 1024 is used to rotate the second magnetic field emission structure 1020 within the second support 1014. In FIG. 11C, the mirror image second magnetic field emission structure 1020 is further rotated by the release mechanism 1024 and the attractive force continues to decrease. In FIG. 11D, the mirror image second magnetic field emission structure 1020 is still further rotated by the release mechanism 1024 until the attractive force becomes very small, such that the two magnetic field emission structures 1018 and 1020 are easily separated as shown in FIG. 11E. One skilled in the art would also recognize that the second end 1016 of the strap 1010 can also be detached from the second support 1014 of the frame 1002 by applying a pull force, shear force, or any other force sufficient to overcome the attractive peak spatial force between tile substantially aligned first and second field emission structures 1018 and 1020. Given the two magnetic field emission structures 1018 and 1020 are held somewhat apart as in FIG. 11E, the two magnetic field emission structures 1018 and 1020 can be moved closer and rotated towards alignment producing a small spatial force as in FIG. 11F. The spatial force increases as the two magnetic field emission structures 1018 and 1020 become more and more aligned in FIGS. 11G and 11H and a peak spatial force is achieved when aligned as in FIG. 11I. It should be noted that the direction of rotation was arbitrarily chosen and may be varied depending on the code employed. Additionally, the mirror image second magnetic field emission structure 1020 is the mirror of the selected first magnetic field emission structure 1018 resulting in an attractive peak spatial force (see also FIGS. 3-4). This way of securing and removing the strap 1010 to and from the frame 1002 is a marked-improvement over the prior art in which the conventional mask had loops, buckles, clamps, hooks, or other known fastening mechanisms which required a great detail of dexterity on the part of the person to use when they want to secure and remove the strap from the frame.

The mask 1000 is described above as having a release mechanism 1024 (e.g., turn-knob 1024) which is used to turn the mirror image second magnetic field emission structure 1020 relative to the selected first magnetic field emission structure 1018 such that the second end 1016 of the strap 1010 can be attached (secured) to or removed from the frame 1002. FIGS. 12A-12C are several diagrams that illustrate an exemplary release mechanism 1024 (e.g., turn-knob 1024) in accordance with an embodiment of the present invention. In FIG. 12A, a portion of the second end 1016 of the strap 1010 which has the series of first magnetic field emission structures 1018 is shown along with a portion of the second support 1014 of the frame 1002 having the second magnetic field emission structure 1020. The second magnetic field emission structure 1020 is physically secured to the release mechanism 1024. The release mechanism 1024 and the second magnetic field emission structure 1020 are also configured to turn about axis 1026 with respect to and within the second support 1014 allowing them to rotate such that the second magnetic field emission structure 1020 can be attached to and separated from the selected first magnetic field emission structure 1018 which enables the strap 1010 and frame 1002 to be connected to and separated from one another. Typically, the release mechanism 1024 and the second magnetic field emission structure 1020 would be turned by the user's hand. The release mechanism 1024 can also include at least one tab 1028 which is used to stop the movement of the second magnetic field emission structure 1020 within the second support 1014 relative to the first magnetic field emission structure 1018. In FIG. 12B, there is depicted a general concept of using the tab 1028 to limit the movement of the second magnetic field emission structure 1020 between two travel limiters 1030*a* and 1030*b* which protrude up from the second support 1014. The two travel limiters 1030*a* and 1030*b* might be any fixed object placed at desired locations on the second support 1014 where for instance they limit the turning radius of the release mechanism 1024 and the second magnetic field emission structure 1020. FIG. 12C depicts an alternative approach where the second support 1014 has a travel channel 1032 formed therein that is configured to enable the release mechanism 1024 (with the tab 1028) and the second magnetic field emission structure 1020 to turn about the axis 1026 where the travel limiters 1032*a* and 1032*b* limit the turning radius. For example, when the tab 1028 is stopped by travel limiter 1032*a* (or travel limiter 1030*a*) then the second end 1016 of the strap 1010 can be separated from the frame 1002, and when the tab 1028 is stopped by travel limiter 1032*b* (or travel limiter 1030*b*) then the second end 1016 of the strap 1010 is secured to the frame 1002.

Figure 13A:
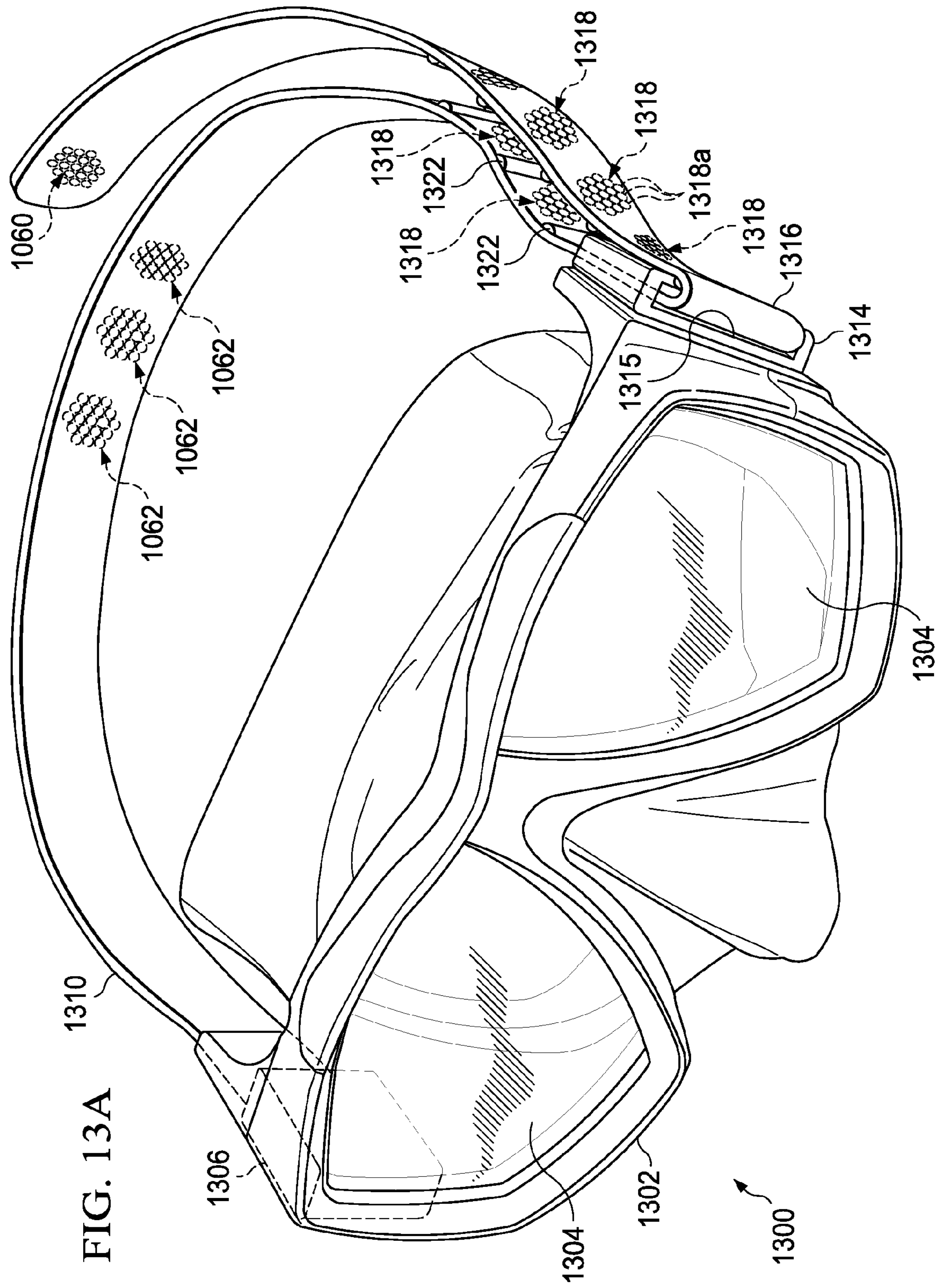
FIGS. 13A-13C are different diagrams of another exemplary correlated magnetic scuba mask in accordance with another embodiment of the present invention.
Figure 13B:
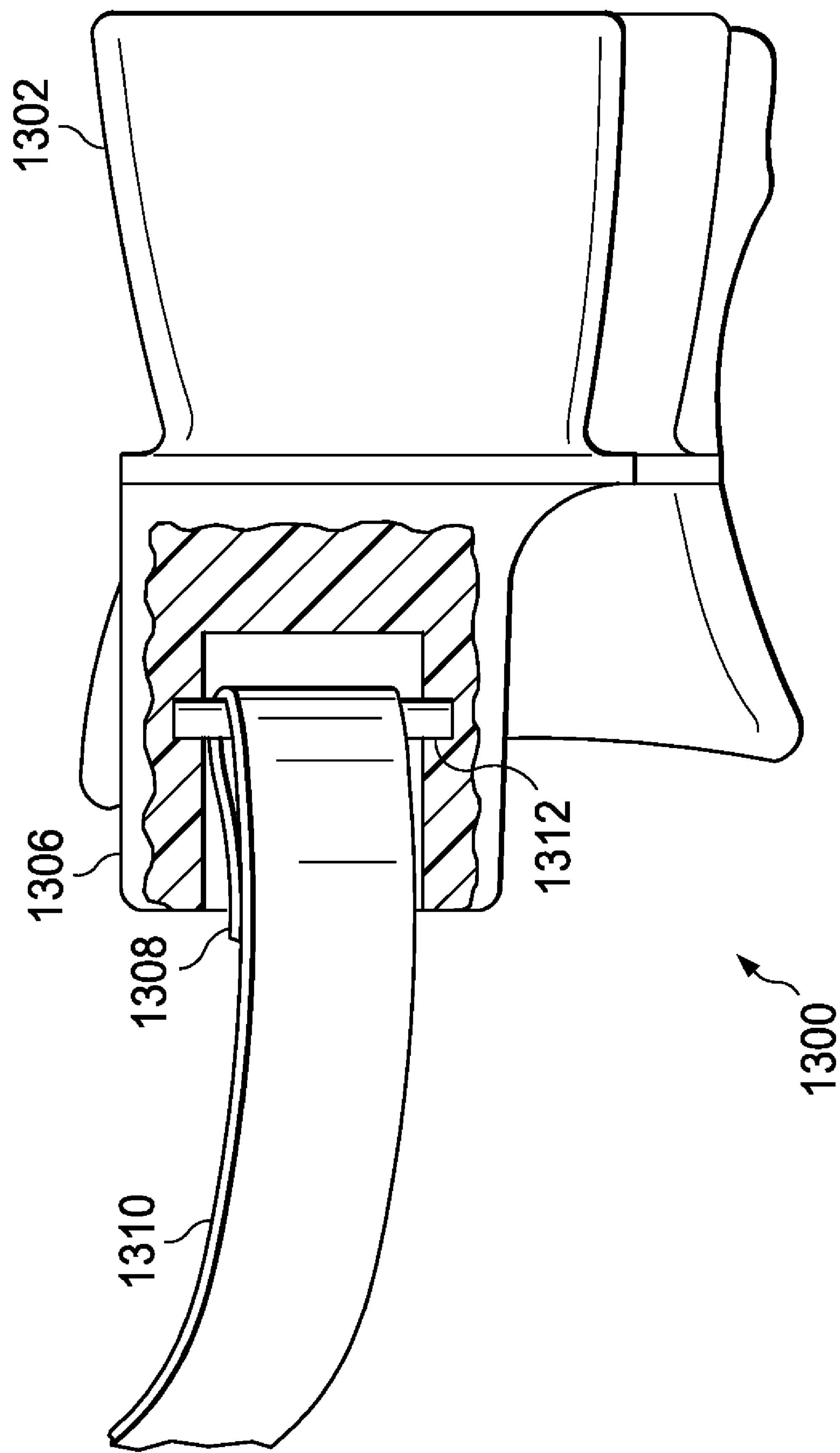
Figure 13C:
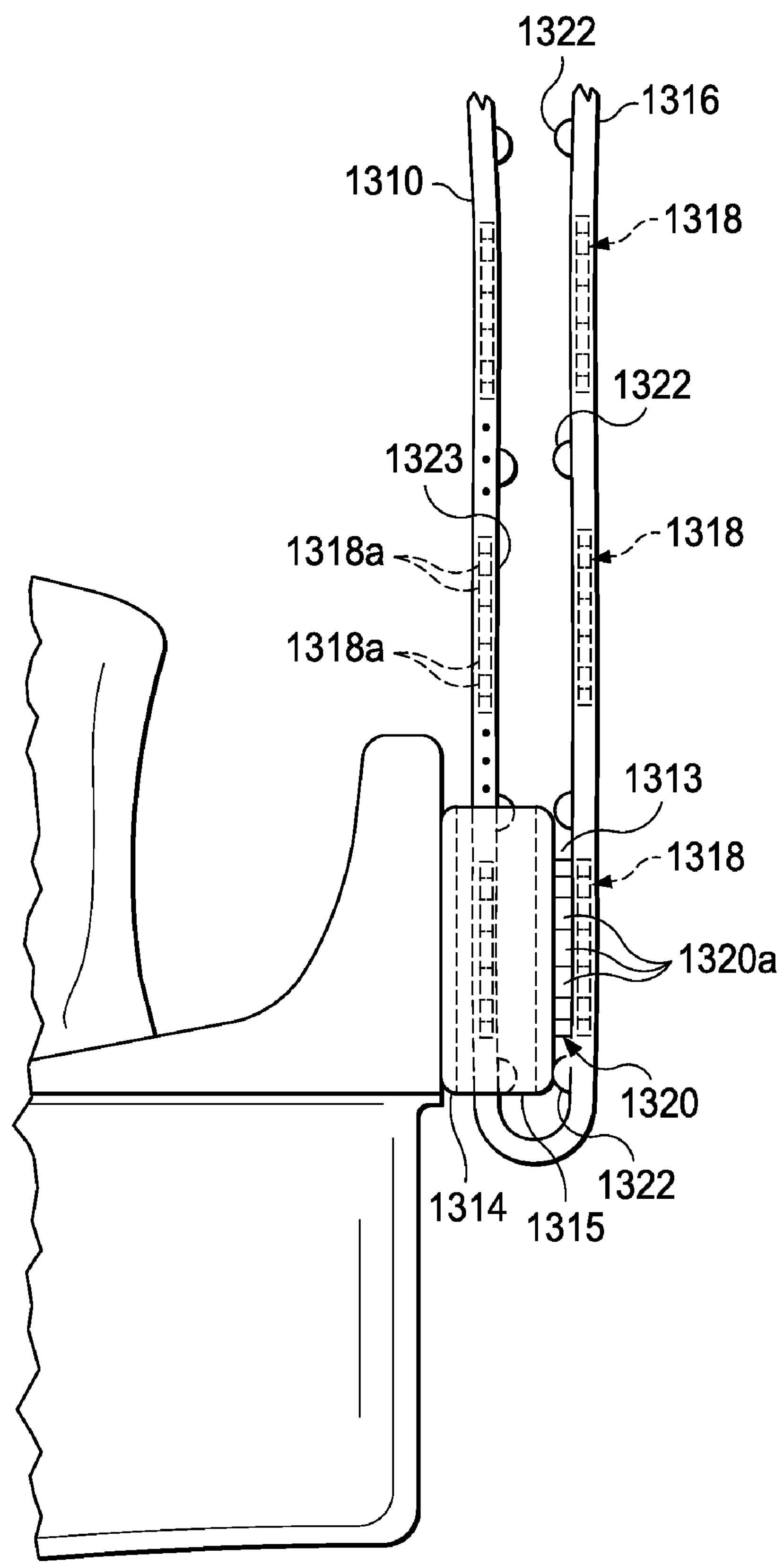

Referring to FIGS. 13A-13C, there are several diagrams of an exemplary correlated magnetic mask 1300 in accordance with another embodiment of the present invention. The correlated magnetic scuba mask 1300 (snorkel mask 1300) includes a frame 1302 which supports one or more transparent lenses 1304 (two shown). The frame 1302 has a first support 1306 at which there is attached thereto one end 1308 of a strap 1310. For instance, the first support 1306 may have a pin 1312 around which is wrapped the first end 1308 of the strap 1310 (see FIG. 13B). The frame 1302 also has a second support 1314 at which a second end 1316 of the strap 1310 can be securely attached thereto or removed therefrom with the aid of correlated magnetic technology (see FIG. 13C).

The strap 1310 has attached thereto (incorporated therein) a series of first magnetic field emission structures 1318 that are located next to one another along a length of the second end 1316. The second support 1314 has attached thereto (incorporated therein) a second magnetic field emission structure 1320 which is exposed to or located within an exterior portion 1313 of the second support 1314 (compare to FIG. 10). The first and second magnetic field emissions structures 1318 and 1320 both have the same code but are a mirror image of one another (see FIGS. 4 and 11). In one embodiment, the strap 1310 has a series of first magnetic field emission structures 1318 anyone of which can interface with and attach to the second magnetic field emission structure 1320 incorporated within the second support 1314 of the frame 1302 such that a person can easily attach the mask 1300 to their head and regulate the length and tension of the strap 1310 around their head. In particular, the second end 1316 of the strap 1310 can be pulled through a hole 1315 in the second support 1314 and wrapped around so as to be attached to the exposed portion 1313 of the second support 1314 on the frame 1302 when a selected first magnetic field emission structure 1318 and the second magnetic field emission structure 1320 are located next to one another and have a certain alignment with respect to one another (see FIG. 11). If desired, the strap 1310 may have transversal ribs 1322 (or other positioning features) extending from one side 1323 thereof which are located between each of the first magnetic field emission structures 1318 where the transversal ribs 1322 can be used to help position the selected first magnetic field emission structure 1318 next to the second magnetic field emission structure 1320.

The person can easily remove the mask 1300 from their head by separating the attached first and second magnetic field emission structures 1318 and 1320. In particular, the strap 1310 can be released from the second support 1314 of the frame 1302 when the selected first magnetic field emission structure 1318 and the second magnetic field emission structure 1320 are turned or misaligned with respect to one another (see FIG. 11). Typically, the person would grab and twist the strap 1310 to misalign and separate the first magnetic field emission structure 1318 from the second magnetic field emission structure 1320. Alternatively, the strap 1310 may have a series of release mechanisms or turn-knobs (not shown) which are secured to the first magnetic field emission structures 1318 and can be used to twist the strap 1310 to misalign and separate the first magnetic field emission structure 1318 from the second magnetic field emission structure 1320. The attachment and de-attachment of the first and second magnetic field emission structures 1318 and 1320 is possible because the first and second magnetic field emission structures 1318 and 1320 each include an array of field emission sources **1318*a* and 1320*a* (e.g., an array of magnets 1318*a* and 1320*a*) each having positions and polarities relating to a desired spatial force function that corresponds to a relative alignment of the first and second magnetic field emission structures 1318 and 1320** within a field domain (see discussion about correlated magnet technology).

If desired, the strap 1310 can have attached thereto (or incorporated therein) a third magnetic field emission structure 1360 at the second end 1316 and at another portion thereof one or more mirror image fourth magnetic field emission structures 1362 can be attached thereto (or incorporated therein). The third magnetic field emission structure 1360 can be attached to one of the fourth magnetic field emission structures 1362 so that the second end 1316 of the strap 1310 does not hang loose when the first and second magnetic field emission structures 1318 and 1320 are attached to one another The third and fourth magnetic field emission structures 1360 and 1362 may be different than and not interact with the first and second magnetic field emission structures 1318 and 1320 but they would function in a similar manner.

The magnetic field structures used in the exemplary correlated masks 1000 and 1300 described previously are themselves exemplary and can be replaced by or used in conjunction with many different types of magnetic field structures to include other two dimensional structures, one dimensional structures, or three dimensional structures, and can be implemented using various forms of field emission sources as have been described herein. Moreover, the approach of putting the second end 1016 and 1316 of a strap 1010 and 1310 through a hole 1015 and 1315 is also exemplary and alternative approaches could be employed where a strap is attached without putting the second end through a hole (i.e., the second end is brought against the second support). Additionally, the length of the strap 1010 and 1310 could be such that the second end 1016 and 1316 of the strap would end at or just past the second support 1014 and 1314 (i.e., the second end would not wrap around the second support).

Generally, the straps 1010 and 1310 of the present invention can also be referred to as adjustable length attachment mechanisms and can be used for attachment purposes in a variety of other applications such as shoe or boot straps, helmet straps, saddle straps, belts, harnesses, cargo tie downs, banding, adjustable-sized hat straps, adjustable sized clothing, and the like. Such straps, or similar correlated magnetic adjustable length attachment mechanisms, can also be configured to function with a correlated magnetic key mechanism such as is described in disclosures that have been previously incorporated by reference. For instance, the use of a correlated magnetic key mechanism would allow an object such as a luggage carrier or canoe on the roof of a vehicle or a cargo container on a ship can be strapped down and the key mechanism removed and later used to release the strap.

Moreover, one skilled in the art will recognize that in alternative approaches to the exemplary correlated mask embodiments 1000 and 1300 previously described, the multiple first magnetic field emission structures 1018 and 1318 could be attached to (or incorporated therein) the second supports 1014 and 1314 which might be made longer than depicted, and the second magnetic field emission structures 1020 and 1320 could be attached to (or incorporated therein) the straps 1010 and 1310.

Furthermore, one skilled in the art will recognize that both ends of a strap 1010 and 1310 could be similarly configured to attach/detach to supports that are similarly configured as the second supports 1014 and 1314 described above thereby enabling either end of the strap 1010 and 1310 to be attached/detached and either end of the strap 1010 and 1310 to be used to "size" the strap around a person's head (or around some other object).

Additionally, such straps 1010 and 1310 can be attached to each other or to other objects, such as to a scuba harness, web belt, tool belt, etc . . . . If desired, straps 1010 and 1310 could attach to an object and then other straps could be attached to them to aid in securing the object. For storage purposes, a strap 1010 and 1310 could also be attached to a wall having an appropriate magnetic field emission structure. Generally, one skilled in the art after reading this document will recognize that various combinations of magnetic field emission structures that can be used to enable attachment of such straps with other straps and with other objects. Similarly, a magnetic field emission structure attached to the scuba mask 1000 and 1300 could be attached to another object, such as wall or a boat.

Although multiple embodiments of the present invention have been illustrated in the accompanying Drawings and described in the foregoing Detailed Description, it should be understood that the present invention is not limited to the disclosed embodiments, but is capable of numerous rearrangements, modifications and substitutions without departing from the invention as set forth and defined by the following claims.

The invention claimed is:

1. A mask comprising:

a frame that supports at least one lens, where the frame has a first support with a first end of a strap attached thereto, where the strap has a second end which incorporates a first field emission structure, where the frame has a second support which incorporates a second field emission structure, where the second end of the strap is attached to the second support of the frame when the first and second field emission structures are located next to one another and have a certain alignment with respect to one another, where each of said first and second field emission structures include field emission sources having positions and polarities relating to a desired spatial force function that corresponds to a relative alignment of the first and second field emission structures within a field domain.

2. The mask of claim 1, wherein the second end of the strap is released from the second support of the frame when the first and second field emission structures are turned with respect to one another.

3. The mask of claim 2, wherein the second support of the frame further includes a release mechanism that turns the second field emission structure with respect to the first field emission structure so as to release or attach the second end of the strap from or to the second support of the frame.

4. The mask of claim 2, wherein the strap further includes a release mechanism that turns the first field emission structure with respect to the second field emission structure so as to release or attach the second end of the strap from or to the second support of the frame.

5. The mask of claim 1, wherein the second end of the strap has incorporated therein a plurality of the first field emission structures any one of which interacts with the second field emission structure attached to the second support of the frame.

6. The mask of claim 1, wherein the strap has incorporated therein a third field emission structure associated with the second end and a fourth field emission structure associated with another portion of the strap, where the third field emission structure interacts with the fourth field emission structure so that the second end of the strap can be attached to the another portion of the strap, where each of said third and fourth field emission structures include field emission sources having positions and polarities relating to a second desired spatial force function that corresponds to a relative alignment of the third and fourth field emission structures within a second field domain.

7. The mask of claim 1, wherein said positions and said polarities of each of said field emission sources are determined in accordance with at least one correlation function.

8. The mask of claim 7, wherein said at least one correlation function is in accordance with at least one code.

9. The mask of claim 8, wherein said at least one code is at least one of a pseudorandom code, a deterministic code, or a designed code.

10. The mask of claim 8, wherein said at least one code is one of a one dimensional code, a two dimensional code, a three dimensional code, or a four dimensional code.

11. The mask of claim 1, wherein each of said field emission sources has a corresponding field emission amplitude and vector direction determined in accordance with the desired spatial force function, wherein a separation distance between the first and second field emission structures and the relative alignment of the first and second field emission structures creates a spatial force in accordance with the desired spatial force function.

12. The mask of claim 11, wherein said spatial force comprises at least one of an attractive spatial force or a repellant spatial force.

13. The mask of claim 11, wherein said spatial force corresponds to a peak spatial force of said desired spatial force function when said first and second field emission structures are substantially aligned such that each field emission source of said first field emission structure substantially aligns with a corresponding field emission source of said second field emission structure.

14. The mask of claim 1, wherein said field domain corresponds to first field emissions from said first field emission sources of said first field emission structure interacting with second field emissions from said second field emission sources of said second field emission structure.

15. The mask of claim 1, wherein said polarities of the field emission sources include at least one of North-South polarities or positive-negative polarities.

16. The mask of claim 1, wherein at least one of said field emission sources include a magnetic field emission source or an electric field emission source.

17. The mask of claim 1, wherein at least one of said field emission sources include a permanent magnet, an electromagnet, an electret, a magnetized ferromagnetic material, a portion of a magnetized ferromagnetic material, a soft magnetic material, or a superconductive magnetic material.

18. A method for using a mask, said method comprising the steps of:

placing the mask on a head of a person, where the mask includes a frame that supports at least one lens, where the frame has a first support with a first end of a strap attached thereto, where the strap has a second end which incorporates a first field emission structure, where the frame has a second support which incorporates a second field emission structure, and pulling the second end of the strap around the head of the person so the first field emission structure interacts with the second field emission structure, where the second end of the strap is attached to the second support of the frame when the first and second field emission structures are located next to one another and have a certain alignment with respect to one another, and where each of said first and second field emission structures include field emission sources having positions and polarities relating to a desired spatial force function that corresponds to a relative alignment of the first and second field emission structures within a field domain.

19. The method of claim 18, further comprising a step of releasing the second end of the strap from the second support of the frame, where the second end of the strap is released from the second support of the frame when the first and second field emission structures are turned with respect to one another.

20. The method of claim 18, further comprising a step of attaching the second end of the strap to another portion of the strap, wherein the strap has incorporated therein a third field emission structure associated with the second end and a fourth field emission structure associated with the another portion of the strap, where the third field emission structure interacts with the fourth field emission structure, where each of said third and fourth field emission structures include field emission sources having positions and polarities relating to a second desired spatial force function that corresponds to a relative alignment of the third and fourth field emission structures within a second field domain.

21. The method of claim 18, wherein the mask is either a medical mask, a laboratory mask, a welding mask, a fencing mask, a goalie mask, a paint mask, a paintball mask, a catcher's mask, a ski mask, a goalie mask, an oxygen mask, a surgical mask, a face shield, a filter mask, a theatrical mask, a costume mask, a continuous positive airway pressure mask, an industrial mask, a military mask, or a scuba mask.

* * * * *